(12) United States Patent
Tomasz et al.

(10) Patent No.: US 6,391,614 B1
(45) Date of Patent: May 21, 2002

(54) AUXILIARY GENE AND PROTEIN OF METHICILLIN RESISTANT BACTERIA AND ANTAGONISTS THEREOF

(75) Inventors: Alexander Tomasz; Herminia De Lencastre, both of New York, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 09/419,163

(22) Filed: Oct. 15, 1999

Related U.S. Application Data

(62) Division of application No. 08/679,635, filed on Jul. 10, 1996, now Pat. No. 5,985,643.
(60) Provisional application No. 60/019,315, filed on Jun. 7, 1996, and provisional application No. 60/001,042, filed on Jul. 10, 1995.

(51) Int. Cl.[7] .................. C12M 1/20; C12M 15/00; C07H 21/02
(52) U.S. Cl. .................. 435/253.2; 435/320.1; 536/23.1
(58) Field of Search .............. 435/253.2, 320.1; 536/23.1

(56) References Cited

FOREIGN PATENT DOCUMENTS

WO     WO 95/16039     6/1995

OTHER PUBLICATIONS

Berger–Bachi (1994) Trends in Microbiol. 2:389–92.
De Lencastre et al. (1994) Antimmicrob. Agent. Chemother. 38:2590–8.
De Lencastre et al. (1994) Eur. J. Clin. Microbiol. Infect. Dis. 13:64–73.
De Lencastre et al. (1994) J. Antimicrob. Chemother. 33:7–24.
Ornelas–Soares et al. (1994) J. Biol. Chem. 269:27246–50.
De Jonge et al. (1993) Antimicrob. Agents Chemother. 37:342–6.
De Jonge et al. (1993) Bacteriol 175:2779–82.
Gustafson et al. (1993) In: Abstracts of the 93rd General Meeting of the American Society for Microbiology, Abs. A–97, p. 18.
Henze et al. (1993) J. Bacteriol. 175:1612–20.
Ornelas–Soares et al. (1993) J. Biol. Chem. 268:26268–72.
Berger–Bachi et al. (1992) Antimicrob. Agents Chemotherapy 36:1367–73.
De Jonge et al. (1992) J. Biol. Chem. 267:11248–54.
De Jonge et al. (1992) J. Biol. Chem. 267:11255–9.
Oshida et al. (1992) J. Bacteriol. 174:4952–9.
De Jonge et al. (1991) J. Bacteriol. 173:1105–10.
De Lencastre et al. (1991) Antimicrob. Agents Chemother. 35:632–9.
Maidhof et al. (1991) J. Bacteriol. 173:3507–13.
Tomasz et al. (1991) Antimicrobial Agents and Chemotherapy 35:124–9.
Matthews et al. (1990) Antimicrobial Agents and Chemotherapy 34:1777–9.
Tomasz, (1990) In: Molecular Biology of the Staphylococci, Novick and Skurray, Eds., VHC Publishers: New York, pp. 565–583.
Murakami et al. (1989) J. Bacteriol. 171:874–9.
Leclercg et al. (1988) New Eng. J. Med. 319:157–61.
Hartman et al. (1986) Antimicrob. Agent. Chemother. 29:85–92.
Beck et al. (1985) J. Bacteriol. 165:373–8.
Berger–Bachi (1983) J. Bacteriol. 154:479–87.
Wu et al., 1996, Microbial Drug Resistance 2(2):277–86.
Kornblum et al., 1986, Eur. J. of Clin. Microbiol. 5(6):714–8.

*Primary Examiner*—Karen Cochrane Carlson
(74) *Attorney, Agent, or Firm*—Klauber & Jackson

(57) ABSTRACT

The present invention is directed to the identification of mutant strains of methicillin resistant bacteria, in particular methicillin resistant *Staphylococcus aureus*, to identify the characteristics of such bacteria and develop drugs that can reverse, inhibit, or reduce bacterial resistance to beta lactam antibiotics, e.g., methicillin. The invention particularly relates to identification of a novel mutant strain of methicillin resistant *S. aureus* that manifests a unique phenotype, having a block in cell wall synthesis at or close to the branch point in hexose metabolism involved in the synthesis of cell wall components. Accordingly, the invention provides for methods of treatment and corresponding pharmaceutical compositions for treating bacterial, particularly staphylococcal, infections.

9 Claims, 12 Drawing Sheets

FIG. 6A

```
EcoRV
   1 ATCGCTTATTTAAAAGCCACTTTTAAAAGCTAATAAAAAGATTAATGGTGACACAAAAGATGTCGCAGAAGTAACGGCTTTTGATAAAAAA        90

91 CTGAATAAATTAAATGTATCGATTCAACCTAATGAATTACAAGTTAAAGTAGAGCCTTTTAGCAAAAAGGTTAAAGTAAATGTT              180

181 AAACAGAAAGGTAGTTTAGCAGATGATAAAGAGTTAAGTTCGATTGATTTAGAAGATAAAGAAATTGAAATCTTCGGTAGTCCGAGATGAC       270

271 TTACAAAATATAAGCGAAGTTGATGCAGAAGTAGATTTAGATGGTATTCAGAATCAACTGAAAAGACTGTAAAAATCAATTTACCAGAA         360
                                                          -35         .
 361 CATGTCACTAAAGCACAACCAAGTGAAACGAAGGCCTTATATAAATGTAAAATAATAGCTAAATTAAAGGAGAGTAAACAATGGGAAAAT        450
                                                    -10    SD       FemR315        M  G  K  Y      4
   1
 451 ATTTGGTACAGACGGAGTAGAGGTGTCGCAAACCAAGAACTAACACACCTGAATTGGCATTTAAATTAGGAAGATACGGTGGCTATGTTC        540
   5  F  G  T  D  G  V  R  G  V  A  N  Q  E  L  T  P  E  L  A  F  K  L  G  R  Y  G  G  Y  V  L      34

541 TAGCACATAATAAAGGTGAAAAACACCCACGTGTACTTGTAGGTCGCGATACTAGAGTTTCAGGTGAAATGTTAGAATCAGCATTAATAG       630
  35  A  H  N  K  G  E  K  H  P  R  V  L  V  G  R  D  T  R  V  S  G  E  M  L  E  S  A  L  I  A     64

631 CTGGTTTGATTTCAATTGGTGCAGAAGTAATGCGATTAGGTATTATTTCAACACCAGGTGTTGCATATTTAACACGCGATATGGGTCAG        720
  65  G  L  I  S  I  G  A  E  V  M  R  L  G  I  I  S  T  P  G  V  A  Y  L  T  R  D  M  G  A  E     94

721 AGTTAGGTGTAATGATTTCAGCCTCTCATAATCCAGTTGCAGATAATAAATTCTTTGGATCAGATGGTTTTAAACTATCAGATG            810
  95  L  G  V  M  I  S  A  S  H  N  P  V  A  D  N  G  I  K  F  F  G  S  D  G  F  K  L  S  D  E    124

810 AACAAGAAAATGAAATTGAAGCATTATTGGATCAAGAAAACCCAGAATTACCAAGACCAGTTGGCAATGATATTGTACATTATTCAGATT       900
 125  Q  E  N  E  I  E  A  L  L  D  Q  E  N  P  E  L  P  R  P  V  G  N  D  I  V  H  Y  S  D  Y    154

901 ACTTTGAAGGGGCACAAAAATATTTGAGCTATTTAAAATCAACAGTAGATGTTAACTTTGAAGGTTTGAAATTGCTTTAGATGGCAA          990
 155  F  E  G  A  Q  K  Y  L  S  Y  L  K  S  T  V  D  V  N  F  E  G  L  K  I  A  L  D  G  A  N    184

961 ATGGTTCAACATCATCACTAGCGCTCTACACATCCTGAAAAATTAGCTGAAAAGTAGTGAAACTAGTGAAACAATTGGATGTAGTCCTGATGGATATAATA  1080
 185  G  S  T  S  S  L  A  P  F  L  F  G  D  L  E  A  D  T  E  T  I  G  C  S  P  D  G  Y  N  I    214

1081 TCAATGAGAAATGTGGCTCTACACATCCTGAAAAATTAGCTGAAAAAGTAGTTGAAACTGAAAGTGATTTTGGGTTAGCATTTGACGGCG        1170
 215  N  E  K  C  G  S  T  H  P  E  K  L  A  E  K  V  V  E  T  E  S  D  F  G  L  A  F  D  G  D    244

1141 ATGGAGACAGAATCATAGCAGCAGATGAGAATGGTCAAATCGTTGACGTGACAGCAATTATGTTTATTATTGGTCAAGAATGCATAAAA        1260
 245  G  D  R  I  I  A  A  D  E  N  G  Q  I  V  D  G  D  Q  I  M  F  I  I  G  Q  E  M  H  K  N    274
```

FIG. 6B

```
1261 ATCAAGAATTGAATAATGACATGATTGTTTCTACTGTTATGAGTAATTTAGTTTTTACAAAGCGCTTGAACAAGAAGGAATTAAATCTA 1350
 275  Q   E   L   N   N   D   M   I   V   S   T   V   M   S   N   L   G   F   Y   K   A   L   E   Q   E   E   G   I   K   S   N   304
                                                                                                               Ω720
1351 ATAAAACTAAAGTTGGCGACAGATATGTAGTAGAAGAAATGCGTCGCGGTAATTATAACTTAGGTGGAGAACAATCTGGACATATCGTTA 1440
 305  E   E   M   R   R   G   N   Y   N   L   G   G   E   Q   S   G   H   I   V   M   K   T   K   V   G   D   R   Y   V   V   334

1441 TGATGGATTACAATACAACTGGTGATGGTTTATTAACTGGTATTCAATTAGCTTCTGTAATAAAATGACTGGTAAATCACTAAGTGAAT 1530
 335  M   D   Y   N   T   T   G   D   G   L   L   T   G   I   Q   L   A   S   V   I   K   M   T   G   K   S   L   S   E   L   364

1501 TAGCTGGACAAATGAAAAATATCCACACAATCATTAATAACGTACGCGTAACAGATAAATATCGTGTTGAAGAAAATGTTGACGTTAAAG 1620
 365  A   G   Q   M   K   K   Y   P   Q   S   L   I   N   V   R   V   T   D   K   Y   R   V   E   E   N   V   D   V   K   E   394

1621 AAGTTATGACTAAAGTTGAAGTAGAAATGAATGGAGAAGGTCGAATTTTAGTAAGACCTTCTGGAACAGAACCATTAGTTCGTGTCATGG 1710
 395  V   M   T   K   V   E   V   E   M   N   G   E   G   R   I   L   V   R   P   S   G   T   E   P   L   V   R   V   M   V   424

1681 TTGAAGCAGCAACTGATGATGAAGATGCTGAAAGATTTGCACACAAATAGCTGATGTGGTTCAAGATAAATGGGATTAGATAAATAATAC 1800
 425  E   A   A   T   D   E   D   A   E   R   F   A   Q   Q   I   A   D   V   V   Q   D   K   M   G   L   D   K   *       451

1801 TGTATTACAAATGAGCCGATGCGTATCGGTTTTTTGTGTTGTGAAAATAATTTATAGTACAAACGTAAAATGATATAAACAAAAT 1890
                                                     ←――――――――――――――――――

1901 AAAAACAAAGTAATCAATATGTAATATAAAATACACTGGTACTCAATATATAATGATGATAAAATTAATTTAATTAGATAGAGTTGCTT 1980

1981 TGTGTTTTTAACGCAGATGCTACTACTACTTATCTTAACAGTTGATTAAGTGAAATCATTTAACACGGAGAATAATCAACCAGGAGGATGACT 2070

2071 TAATGAATTTATTCAGACAACAAAAATTTAGTATCAGAAAATTTAATGTCGGTATTTTTTCAGCTTTAATTGCCACTGTTACTTTTATAT 2160
                                                                                        ―――――――――――→
2161 CTACTAACCCGACAACAGCCGTCTGCAG 2187
                                PstI
```

FIG. 7A

```
                   10                  20                  30                  40                  50                  60
FemR315    -------------------- -------------------- MGKYFGTDGVRGVANQELTPELAFKLGRYGGYVLAHNKGEKHPRVLVGR
HpUreC     -------------------- -------------------- -MKIFGTDGVRGKAGVKLTPMFVMRLGIAAG--LYFKKHSQTNKILIGK
MlUreD     -------------------- -------------------- -MGRLFGTDGVRGVANRELTPELVLALGAAAARCLANSGEPGRRVAVIGR
EcoPGM     -------------------- -------------------- --MKKLTCFKAYDIRGKLGEELNEDIAWRIGRAYGEFL------KPKTIVLGG
PaPMM      -------------------- -------------------- --MTKLTCFKAYDIRGRLGEELNEDIAWRIGRAYGEYL------KPKTVVLGG
RmPGM      VKIVTVKTKAYPDQKPGTSGLRKRVKVFQSSTNYAENFIQSIISTVEPAQRQEATLVVGG 70                  80                  90                 100                 110                 120
FemR315    DTRVS-GEMLESAL-IAGLISIGAEVM-RLGIISTPGVAYLTRDMGAELGVMISASHNPV
HpUreC     DTRKS-GYMVENAL-VSALTSIGYNVI-QIGPMPTPAIAFLTEDMRCDAGIMISASHNPF
MlUreD     DPRAS-GEMLEAAV-IAGLTSAGVDAL-RVGVLPTPAVAYLTGAYDADFGVGGIEVTASHNPM
EcoPGM     DVRLT-SETLKLAL-AKGLQDAGVDVL-DIGMSGTEEIYFATFHLGVDGGIEVTASHNPM
PaPMM      DVRLT-SEALNVAL-AKGLQDAGVDVL-DIGMSGTEEIYFATFHLGVDGGIILTASHNPM
RmPGM      DGRFYMKEAIQLIVRIAAANGIGRLVIGQNGILSTPAVSCIIRRKIKAIGGIILTASHNPG
                                                                                                                      a 130                 140                 150                 160                 170                 180
FemR315    ADN---GIKFFGSDGFKLSDEQE-N--EIEAALL-DQEN-PELPRPVGNDIVHYSDYFEGA
HpUreC     EDN---GIKFFNSYGYKLKEEEE-R--AIEEIFHDEGL-LHSSYKVGESVGSAKRIDDVI
MlUreD     VDN---GIKIFGPGGHKLDDDTE-D--QIEDLV--TGG-RPAGVAIGRVIDAEDAT
EcoPGM     DYN---GMKLVREGARPISGDTGLR--DVQRLAEANDF-PPVDETKRGRYQQINLRDAYV
PaPMM      DYN---GMKLVREGARPISGDTGLR--DVQRLAEAGDF-PPVNEAARGSYRQISLRDAYI
RmPGM      GPNGDFGIKFNISNGGPAPEAITDKIFQISKTIEEYAICPDLKVDLGVLGKQQFDLENKF 190                 200                 210                 220                 230                 240
FemR315    QKYLSYLKSTVD--VNFEGLKIALDGANGSTSSLAPFLFG-----DLEADTETIGCSPD
HpUreC     GRYIAHLKHSFPKHLNLQSLRIVLDTANGAAYKVAPVVFS-----ELGADVLVINDEPN
MlUreD     ERYLRHVGKAST--IRLDGLTVVDCAHGAASSAPRAYR------AAGARVIAINADPN
EcoPGM     DHLFGYINVKNLTPLKLVINSGNGAAGPVVDAIEARFKAL-----GAPVELIKVHNTPD
PaPMM      DHLLGYISVNNLTPLKLVFNAGNGAAGPVIDAIEARLKAL-----GAPVEFIKIHNTPD
RmPGM      KPFTVEIVDSVEAYATMLRNIFDFNALKELLSGPNRLKIRIDAMHGVVGPYVKKILCEEL
```

FIG. 7B

```
              250             260             270             280             290             300
FemR315  GYNINEKC-------  GSTHPE----  KLAEKVVET---  ESDFGLAPDGDDR  IIAADENG
HpUreC   GCNINEQC-------  GALHPN----  QLSQEVKKY---  RADLGFAPDGDADR  CLVVDNLG
MlUreD   GININDRC-------  GSTDLG----  SLRSAVLAH---  RADLGLAPDGDADR  CFLFDENG
EcoPGM   GNFPNGIP-------  NPLLPECRDDTRNAVIKH---  GADMGIAPDGDFDR  CFLFDEKG
PaPMM    GTFPNGIP-------  NPLLPECRDDTRKAVIEH---  GADMGIAPDGDFDR  CFLFDEKG
RmPGM    GAPANSAVNCVPLEDFG  GHHPDPNLTYAADLVETMKSGEHDFGAAPDGDDR  NMLGKHG b 310             320             330             340             350             360
FemR315  QIVDGDQIMFIIGQEMHKN---  QELNNDMIVSTVMSNLGFYKALEQEGIKSNKTKVGDRY
HpUreC   NIVHGDKLLGVLGVYQKSK---  NALSSQAIVATNMSNLALKEYLKSQDLEKHCAIGDKF
MlUreD   DLVDGDAIMVVLALAMQEA---  GELSSNTLVTTVMSNLGLHLAMRSVGVIVRTTDVGDRY
EcoPGM   QFIEGYYIVGLLAEAFLEK---  NP-GAKIIHDPRLSWNTVDVTAAGGTPV-MSKTGHAF
PaPMM    QFIEGYYIVGLLAEAFLEK---  HP-GAKIIHDPRLTWNTEAVVTAAGGTPV-MSKTGHAF
RmPGM    FFVNPSDSVAVIAANIFSIPYFQQTGVRGFARSMPTSGALDRVANATKIALYSTPTGWKF c 370             380             390             400             410             420
FemR315  VVEEMRRGNYNLGGEQSGHIVMMDYNTTGDGLLTGIQLASVIKMTGKSLSELAGQ-----
HpUreC   VSECMRLNKANFGGEQSGHIIFSDYAKTGDGLVCALQVSALVLESKLVSSVRLNP-----
MlUreD   VLEELRAGDFSLGGEQSGHIVMPALGSTGDGIHITGLRLMTRMVQTSSLAALASA-----
EcoPGM   IKERMRKEDAIYGGEMSAHHYFRDFAYCDSGMIPWLLVAELVCLKDKTLGELVRD-----
PaPMM    IKERMRTEDAIYGGEMSAHHYFRDFAYCDSGMIPWLLVAELVCLKRQSLGELVRD-----
RmPGM    FGNLMDASKLSLCGEESFGTG-SDHIREKDGLWAVLAWLSILATRKQSVEDILKDHWHKF e 430             440             450             460             470             480
FemR315  ---------------  MKKYPQSLINVRVTDKYRVEAN-------  VDVKE-VMTKVE-----
HpUreC   ---------------  FELYPQNLVNLNVQKKPPLESL------  KGYNA-LLKELD-----
MlUreD   ---------------  MRALPQVLINVEVADKTTAAAA------  PLVQT-AVETAE-----
EcoPGM   ---------------  RMAAFPASGEINSKLAQPVEAI------  NVEQH-FSREAL-----
PaPMM    ---------------  RMAAFPASGEINSRLAEPAAAI------  ARVEAHFAEEAQ-----
RmPGM    GRNFFTRYDYEEVEAEGATKMMKDLEALMFDRSFVGKQFSANDKVYTVEKADNFEYHDPV
```

FIG. 7C

```
              490        500        510        520        530        540
FemR315   --VEMNGEGRILVRPSGTEPLVRV-----MVEAATDEDAERFAQQIADVVQDK-------------
HpUreC    ----KLEIRHLIRYSGTENKLRI-----LLEAKDEKLLESKMQELKEFFEGH-------------N---
MlUreD    --VELGNTGRILLRPSGTEPMIRV-----MVEAAEEDVAHRVATRVAAAVSAQGSPLRCWN------
EcoPGM    --AVDRTDGISMTFADWRFNLRTS---NTEPVVRLNVESRGDVPLMEARTRTLL-------------
PaPMM     --AVDRTDGLSMSFADWRFNLRSS---NTEPVVRLNVESRGDIPLMEARTRTLL-------------
RmPGM     DGSVSKNQGLRLIFADGSRIIFRLSGTGSAGATIRLYIDSYEKDNAKINQDPQVMLAPLI 550        560
FemR315   ------MGLDK----------------
HpUreC    ------LC-------------------
MlUreD    PDAISGVELRL----------------
EcoPGM    ------TLLNE----------------
PaPMM     ------ALLNQ----------------
RmPGM     SIALKVSQLQERTGRTAPTVIT
```

FIG. 8

```
FemR315    93  AELGVMISASHNPVADNGIKF  113
               |  |:::.||||| .:.||                a
RmPGM     107  AIGGIILTASHNPGGPNGDFG  127

FemR315   216  EKCGSTHPEK  225
               |. |: ||:.                          b
RmPGM     254  EDFGGHHPDP  263

FemR315   236  DFGLAFDGDGDRII  249
               ||| ||||||||| :                     c
RmPGM     281  DFGAAFDGDGDRNM  294

FemR315   320  GNYNLGGEQSGHI  332
               :...|.||:| .                        d
RmPGM     368  SKLSLCGEESFGT  380

FemR315   339  TTGDGLLTGI  348
               . |||:..:                           e
RmPGM     386  REKDGLWAVL  395
```

AUXILIARY GENE AND PROTEIN OF METHICILLIN RESISTANT BACTERIA AND ANTAGONISTS THEREOF

RELATED APPLICATIONS

This application is a divisional of Ser. No. 08/679,635 filed Jul. 10, 1996, now U.S. Pat. No. 5,985,643, which claims priority to provisional applications Ser. No. 60/001,042, filed Jul. 10, 1995 and 60/019,315 filed Jun. 7, 1996.

The research leading to the instant Application was supported by National Institutes of Health Grant No. RO1 A116794. The Government may have certain rights in the invention.

FIELD OF THE INVENTION

The present invention relates to the identification of auxiliary genes that encode proteins involved in antibiotic resistance in bacteria, and to compounds that can antagonize the activity of such proteins, thereby resensitizing resistant bacteria to antibiotics.

BACKGROUND OF THE INVENTION

Clinical-Epidemiological Background

Methicillin resistant strains of *Staphylococcus aureus* (MRSA) have become first ranking nosocomial pathogens worldwide. These bacteria are responsible for over 40% of all hospital-born staphylococcal infections in large teaching hospitals in the US. Most recently they have become prevalent in smaller hospitals (20% incidence in hospitals with 200 to 500 beds), as well as in nursing homes (Wenzel et al., 1992, Am. J. Med. 91(Supp 3B):221–7). An unusual and most unfortunate property of MRSA strains is their ability to pick up additional resistance factors which suppress the susceptibility of these strains to other, chemotherapeutically useful antibiotics. Such multiresistant strains of bacteria are now prevalent all over the world and the most "advanced" forms of these pathogens carry resistance mechanisms to all but one (vancomycin) of the usable antibacterial agents (Blumberg et al., 1991, J. Inf. Disease (63:1279–85).

A most ominous and recent development is the appearance of a vancomycin resistance mechanism in another nosocomial pathogen—*Enterococcus faecium*—which is known for its ability to transfer from one cell to another plasmid-born resistance factors, such as vancomycin resistance. The arrival of vancomycin resistance to MRSA is only a matter of time. Once this happens, an invasive bacterial pathogen without any antibacterial agent to control it will result. This event would constitute nothing short of a potential public health disaster of immense proportion (Leclercg et at., 1988, New Eng. J. Med. 319:157–61).

The preceding explains the intense interest in the public health and pharmacological community in any new method that promises a usable intervention against MRSA. A more complete explanation of the basis for antibiotic resistance follows.

Molecular Basis of Antibiotic Resistance

The central genetic element of methicillin resistance is the so called mecA gene. This gene is found on a piece of DNA of unknown, non-staphylococcal origin that the ancestral MRSA cell(s) must have acquired from a foreign source. The mecA gene encodes for a penicillin binding protein (PBP) called PBP2A (Murakami and Tomasz, 1989, J. Bacteriol. 171:874–79), which has very low affinity for the entire family of beta lactam antibiotics. In the current view, PBP2A is a kind of "surrogate" cell wall synthesizing enzyme that can take over the vital task of cell wall synthesis in staphylococci when the normal complement of PBPs (the normal catalysts of walt synthesis) can no longer function because thy have become fully inactivated by beta lactam antibiotic in the environment. The critical nature of the mecA gene and its gene product PBP2A for the antibiotic resistant phenotype was best demonstrated by transposon inactivation experiments in which the transposon Tn551 was maneuvered into the mecA gene. The result was a dramatic drop in resistance level from the minimum inhibitory concentration (MIC) value of 1600 µg/ml in the parental bacterium to the low value of about 4 µg/ml in the transposon mutant (Matthews and Tomasz, 1990, Antimicrobial Agents and Chemotherapy 34:1777–9).

This observation is consistent with the foregoing theory. The mutant bacteria with their interrupted mecA gene could no longer synthesize PBP2A; thus the surrogate enzyme needed for the survival in the antibiotic-rich environment was no longer available to catalyze wall synthesis. Consequently, the methicillin susceptibility of the Tn255 mutant dropped to a level approaching the susceptibility of staphylococci without the mecA gene. Methicillin MIC for such bacteria is usually in the vicinity of 1–2 µg/ml.

Auxiliary Genes

Additional genetic work resulted in several surprising observations. First it was found that the level of antibiotic resistance could also be dramatically lowered in transposon mutants in which the Tn551 did not interrupt the mecA gene or interfere with the expression of this gene (i.e., the production of PBP2A). Clearly, these mutants were low in resistance for some reason other than an interruption of the functioning of the mecA gene. In fact, it turned out that the great majority of Tn551 insertional mutants with reduced methicillin resistance all continued to produce normal amounts of PBP2A in spite of the fact that their resistance level could be reduced by very large factors, such as dropping from the methicillin MIC of 1600 µg/ml to a low of 3 µg/ml.

The first such mutant was isolated in 1983 by Swiss scientists at a time when the nature of methicillin resistance was hardly understood at all (Berger-Bächi, 1983, J. Bacteriol. 154:479–87). Subsequent work in several laboratories have increased the number of these genetic determinants, the common feature of which was that they had an intact mecA gene and yet they had reduced resistance levels to the beta lactam family of antibiotics. The provisional name "auxiliary genes" was proposed for this class of unusual genetic elements to imply that they appeared to perform some essential "helper" function(s) in the expression of high level beta lactam resistance (Tomasz, 1990, In *Molecular Biology of the Staphylococci*, Novick and Skurray, Eds., VHC Publishers: New York, pp. 565–583).

A second surprising observation concerned the number of auxiliary genes that have been identified. By 1993, the number of genetically distinct auxiliary mutants described in the literature had risen to four; presently, six have been identified [Berger-Bächai, *Trends in Microbiology*, 2:389–392 (1994); DeLencastre et al., *J. Antimicrob. Chemother.* 33:7–24 (1994); Henze et al., *J. Bacteriol.* 175: 1612–1620 (1993); Maidhof et al., *J. Bacteriol.* 173:3507–3513 (1991)].

A third set of observations provided clues as to the biochemical nature of auxiliary functions. It was shown by a newly developed high resolution chromatography technique that many of the auxiliary mutants produced abnormal peptidoglycan in their cell walls. Studies combining High Performance Liquid Chromatography (HPLC) and mass spectrometry allowed the identification of the chemical changes that occurred in the mutants (De Jonge et al., 1991, J. Bacteriol. 173:1105–10; De Jonge et al., 1992, J. Biol. Chem. 267:11248–54; De Jonge et al., 1992, J. Biol. Chem 267:11255–9; and De Jonge et al., 1993, J. Bacteriol. 175:2779–82). The cell wall peptidoglycan of auxiliary mutants was composed of muropeptides (cell wall building blocks) either with incomplete cross-linking peptides or containing a free glutamic acid residue instead of the usual isoglutamine. Still other mutants showed different cell wall muropeptide fingerprints in which the exact nature of changes remains to be elucidated. These findings suggest that the auxiliary genes are genes involved with the biosynthesis of cell wall precursor muropeptides.

While all the numerous auxiliary mutants share the common feature of carrying an intact mecA, each one of the auxiliary genes are unique by the criteria of (i) physical location on the chromosome as determined by restriction mapping; (ii) in the several cases in which DNA sequences of the genes were determined (as in the cases of the auxiliary genes known as femA, femB and femC) (Berger-Bächi et al., 1992, Antimicrobial Agents and Chemotherapy 36:1367–73; Gustafson et al., 1993, In *Abstracts of the 93rd General Meeting of the American Society for Microbiology*, Abstract A-97, p. 18; and De Lencastre et al., 1993, "Molecular Aspects of Methicillin resistance in *Staphylococcus aureus*", J. Antimicrob. Chemother. 33:), the genes were shown to have unique DNA sequences; and (iii) in the cases in which the mutants had altered cell wall composition, the HPLC patterns provided additional gene-specific fingerprints characteristic of the particular mutant.

Recently, a new tranposon library constructed in the background of the highly and homogeneously methicillin resistant *Staphylococcus aureus* (MRSA) strain COL yielded 70 independent insertional mutants with reduced levels of antibiotic resistance, out of which only two were inserts in mecA while the rest were scattered over seven of the sixteen SmaI fragments of the COL chromosome. Preliminary studies suggest that this library includes at least 10 to 12 new genetic determinants, each of which is needed for optimal expression of methicillin resistance [International Patent Publication No. WO 95/16039, published Jun. 15, 1995 by DeLencastre and Tomasz; DeLencastre and Tomasz, *Antimicrob. Agents. Chemother*. 38:2590–2598 (1994)].

The citation of any reference herein is not an admission that such reference is available as prior art to the instant invention.

SUMMARY OF THE INVENTION

The present invention is broadly directed to the identification of a new auxiliary gene encoding a protein associated with antibiotic resistance in bacteria, in particular Gram positive bacteria, to characterizing the phenotype of bacteria having a mutation in this auxiliary gene, and to identifying compounds that can mimic the phenotype of bacteria in which the activity of the auxiliary gene is disrupted.

In a preferred aspect, the invention is directed to a mutant antibiotic-resistant *Staphylococcus aureus* strain characterized by increased sensitivity to an antibiotic to which a parent of the mutant strain is resistant, and location of the mutation in a SmaI-I fragment of the chromosome of *S. aureus*. Generally, the antibiotic is a beta lactam antibiotic, in particular, methicillin. In a preferred aspect, the mutation is caused by insertion of transposon Tn551.

In a specific embodiment, characterized by RUSA315, the mutation results in a blockade of cell wall synthesis at or close to the branch point in hexose metabolism involved in the synthesis of cell wall components.

The invention is further directed to a DNA molecule comprising a nucleic acid sequence which encodes a protein associated with antibiotic resistance in a *S. aureus* bacterium, which nucleic acid sequence is preferably located in the SmaI-I fragment of the chromosome of the *S. aureus* bacterium. In particular, the DNA molecule comprises in gene, a mutation which results in a blockade of cell wall synthesis at or close to the branch point in hexose metabolism involved in the synthesis of cell wall components. The compositional change of peptidoglycan in a mutant of the invention is the complete disappearance of the unsubstituted disaccharide pentapeptide monomer. In a specific embodiment, the mutant corresponds to RUSA315. In a still further embodiment, the gene has a nucleotide sequence as depicted in FIG. 6 (SEQ ID NO: 1).

The invention is also directed to a recombinant vector comprising the DNA molecule described above, operatively associated with an expression control sequence, and to a bacterial cell comprising the recombinant vector.

In another aspect, the invention is directed to a method for identifying a compound useful for sensitizing bacteria to an antibiotic to which the bacterium is resistant, comprising identifying a compound that antagonizes the activity of a protein associated with antibiotic resistance in a *S. aureus* bacterium, which protein is preferably encoded by a nucleic acid sequence located in the SmaI-I fragment of the chromosome of the *S. aureus* bacterium. Preferably, the protein is involved in synthesis of cell wall components derived from hexose. In a preferred aspect of the invention, the composition and structure of the bacterial cell wall can be analyzed by high performance liquid chromatography and mass spectrometry to determine the association of the protein with muropeptide precursor synthesis. In a specific embodiment, the invention relates to identification of a compound the administration of which results in lack of unsubstituted disaccharide pentapeptide monomer in the bacterial cell wall. This embodiment of the invention relates to identification of a compound the administration of which results in lack of hexose-derived cell wall precursors.

In another specific embodiment, the invention contemplates reducing beta lactam antibiotic resistance in bacteria by administration of a competitive inhibitor antagonist of an enzyme or enzymes involved in synthesis of cell wall compounds derived from hexose.

In yet another aspect, the invention relates to a method for treating a subject suspected of having a bacterial infection comprising administering to the subject an amount of a compound useful for sensitizing the bacteria to an antibiotic to which the bacterium is resistant in conjunction with an amount of the antibiotic sufficient to neutralize the bacteria. Preferably, the compound inhibits or antagonizes the activity of a protein associated with muropeptide precursor synthesis, in particular the synthesis of cell wall compounds derived from hexose.

Accordingly, the invention also relates to a pharmaceutical composition for use in treating a subject suspected of halving a bacterial infection comprising a compound in an amount effective to sensitize bacteria to an antibiotic to which the bacteria are resistant and a pharmaceutically effective carrier. In a further embodiment, the, pharmaceutical composition also comprises an antibiotic in an amount sufficient to neutralize the bacteria.

Although not intending to bound by any particular mechanistic theory or hypothesis, the inventors believe that in the presence of a beta lactam antibiotic the drug molecules and molecules of the cell wall building blocks (muropeptides) compete for the active site of PBP2A, i.e., the surrogate enzyme that, under these conditions, is solely responsible for cell wall biosynthesis. Intact, functioning auxiliary genes allow the production of all the normal cell wall precursor muropeptides, which are highly effective in the competition for the enzyme active site. Thus, in such a staphylococcal cell, relatively higher concentration of the antibiotic is needed for the inactivation of PBP2A, driving the antibiotic MIC value up.

In contrast, inactivated auxiliary genes may prevent the formation of structurally normal cell wall precursors in appropriate intracellular concentrations. Such structurally abnormal—or concentration-wise inadequate—cell wall precursors do not have high enough affinity for the active site of PBP2A., Thus, the relative effectiveness of the drug molecules increases, driving the MIC value down.

However, the identification of strains mutated in auxiliary genes which do not appear to be directly associated with muropeptides precursor synthesis suggests that there are interacting cellular pathways involved in antibiotic resistance.

It is a particular advantage of the invention that the compounds of the invention make possible the use of the known battery of antibiotics, rather than requiring development of new antibiotics, for the treatment of bacterial infections.

The primary object of the invention is to identify compounds that reverse antibiotic resistance in bacteria. These compounds can be used in conjunction with the antibiotics to treat bacterial infections not otherwise amenable to chemotherapy.

Thus, it is an object of the present invention to identify auxiliary genes encoding proteins directly or indirectly associated with antibiotic resistance in bacteria.

It is also an object of the invention to identify such auxiliary genes that encode proteins involved with cell wall precursor synthesis.

Yet another object of the invention is to isolate, sequence and characterize such genes, in order to evaluate the functional activity of the protein encoded by the gene.

It is yet a further object to prepare such proteins in purified form for structural and functional analysis.

Most importantly, it is an object of the invention to screen for and select compounds that reverse antibiotic resistance of bacteria.

These and further objects of the invention will become more clear after consideration of the following FIGURES and DETAILED DESCRIPTION.

BRIEF DESCRIPTION OF THE DRAWINGS

FIG. 6. Nucleotide sequence of the 2187 bp EcoRV-PstI fragment containing femR315 coding region (SEQ ID NO:1). Numbering starts at the ½ EcoRV site and ends at the PstI site (position 2187). The putative start codon is located below the gene designation and the stop codon is designated with an asterisk. A putative Shine-Dalgarno (S.D.) sequence is underlined. The possible candidate for promoter sequences (−35 and −10 regions) is shown. Inverted repeat sequences are indicated by arrows. The insertion site of Tn551 is shown. Amino acids deduced from the nucleotide sequences are specified by standard one-letter abbreviations (SEQ ID NO:2).

FIG. 7. Multiple amino acid sequence alignment of FemR315 with *Helicobacter pylori* UreC(HpUreC) (SEQ ID NO:3), *Mycobacterium leprae*UreD (M1UreD) (SEQ ID NO:4), *Escherichia coli* PGM (EcoPGM) (SEQ ID NO:5) and Pseudomonas aeruginosa PMM(PaPMM) (SEQ ID NO:6). The amino acid stretches in the boxes are known to be critical for PGM activity based on the study on rabbit muscle PGM (SEQ ID NO:7). These stretches are identical or highly homologous among the sequences shown.

FIG. 8. Comparison of the FemR3l5 amino acid sequences with rabbit muscle PGM protein sequences in the key regions. (A) The 21 amino acid long active site region including $Ser^{116}$ stretch. (B) $His^{260}$ flap. (C) Metal binding loop and anchoring residues. (D) $Ser^{377}$ flap. (E) $Lys^{388}$ flap. The bold letters are the amino acids stretches critical for PGM activity. The vertical bars indicate identical amino acids and colons and periods indicate two degrees of similarity of amino acids.

DETAILED DESCRIPTION OF THE INVENTION

Figure 1A:
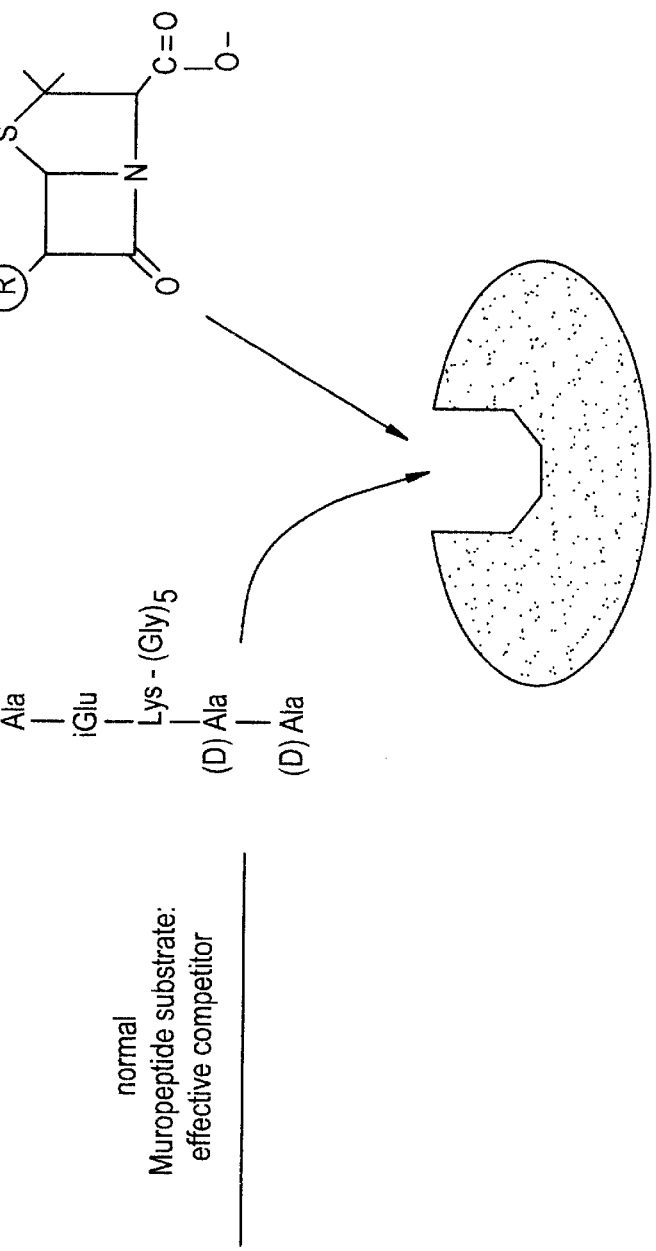
FIG. 1. (Prior Art) Proposed model for competition for the active site of penicillin binding protein (PBP) 2A by cell wall precursor muropeptides and antibiotic. (A) Structurally normal precursors are effective competitors driving the methicillin MIC value up. (B) Precursors with abnormal chemical structure, produced in auxiliary mutants, are ineffective competitors with methicillin, resulting in reduced MIC value (and abnormal cell wall composition). The invention is not intended to be limited by this model, which is offered by way of explanation and not limitation. See WO 95/16039, supra.
Figure 1B:
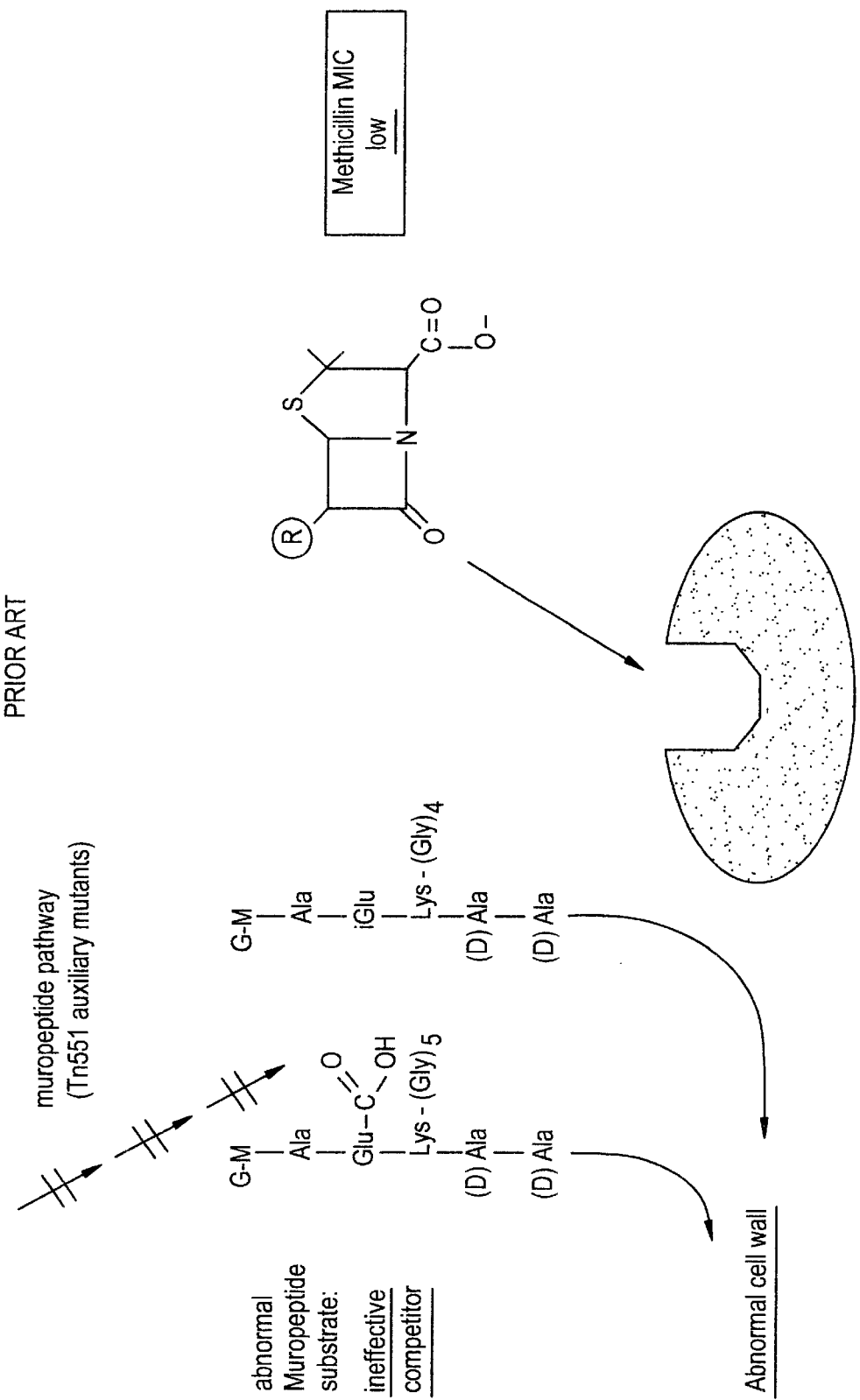

In accordance with the present invention there may be employed conventional molecular biology, microbiology, and recombinant DNA techniques within the skill of the art. Such techniques are explained fully in the literature. See, e.g., Sambrook, Fritsch and Maniatis, "Molecular Cloning: A Laboratory Manual," Second Edition (1989) Cold Spring Harbor Laboratory Press, Cold Spring Harbor, N.Y. (herein "Sambrook et al., 1989"); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)];, "Animal Cell Culture" [R. I. Freshney, ed. (1986)]; "Immobilized Cells And Enzymes" [IRL Press, (1986)]; B. Perbal, "A Practical Guide To Molecular Cloning" (1984). Each of these references is specifically incorporated herein by reference.

Therefore, if appearing herein, the following terms shall have the definitions set out below.

A "replicon" is any genetic element (e.g., plasmid, chromosome, virus) that functions as an autonomous unit of DNA replication in vivo, i.e., capable of replication under its own control.

A "vector" is a replicon, such as plasmid, phage or cosmid, to which another DNA segment may be attached so as to bring about the replication of the attached segment.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid.

A "clone" is a population of cells derived from a single cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see 25 Sambrook et al., supra, 9.50–9.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for, or identical stretch of, a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.: in a more preferred embodiment, the $T_m$ is 65° C. "Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination. A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then translated into the protein encoded by the coding sequence.

An "antisense nucleic acid" is a single stranded nucleic acid molecule which, on hybridizing with complementary bases in an RNA or DNA molecule, inhibits the latter's role. If the RNA is a messenger RNA transcript, the antisense nucleic acid is a countertranscript or mRNA-interfering complementary nucleic acid. As presently used, "antisense" broadly includes RNA-RNA interactions, RNA-DNA interactions, ribozymes and RNase-H mediated arrest. Antisense nucleic acid molecules can be encoded by a recombinant gene for expression in a microorganism, or alternatively they can be prepared synthetically.

A mutant bacterium "corresponds to" the mutant strain of the invention, RUSA315, when it contains any mutation in the femR315 gene or locus that affects expression of a functional FemR315 protein.

A composition comprising "A" (where "A" is a single protein, DNA molecule, vector, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least 90% by weight of the A+B species in the composition, most preferably at least 99% by weight. It is also preferred that a composition, which is substantially free of contamination, contains only a single molecular weight species having the activity or characteristic of the species of interest.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions.

In its primary specific aspect, the present invention relates to a new S. aureus mutants, in which the methicillin MIC value of the paternal MRSA strain COL (MIC 1600 µg/ml) is reduced to between 200 µg/ml and 1.5 µg/ml. This Mutation is located on the chromosomal fragments generated by the restriction nuclease. SmaI. Other mutations have been found on SmaI-C, D, E, and F, and novel mutations on SmaI-A and I. The mutants are distinct by physical mapping using restriction endonucleases, such as but not limited to PstI, EcoRI, EcoRV, and HindIII. RUSA315 appears to be involved in the synthesis of cell wall compounds at a branch point of hexose metabolism. In a specific embodiment, the mutation characteristic of RUSA315 reduces the MIC value from 1600 µg/ml to about 12 to about 25 µg/ml.

Accordingly, in a specific embodiment, the invention relates to identification of an auxiliary gene of staphylococcus that encodes a phosphoglucomutase-like protein with a high degree of similarity or homology to hexoisomerase or hexosamine isomerase, or both, and may be close to the branch point in hexose metabolism where specific cell wall compounds are beginning to be made.

Isolation, Cloning, Expression and Characterization of Auxiliary Genes

Any Gram positive bacterial cell potentially can serve as the nucleic acid source for the molecular cloning of an auxiliary gene of the invention. The nucleic acid sequences can be isolated from *Streptococcus, Bacillus*, Mycobacterium, Staphylococcus, Enterococcus, and other Gram positive bacterial sources, etc. In a specific embodiment, the auxiliary gene is found in staphylococci. The DNA may be obtained by standard procedures known in the art from cloned DNA (e.g., a DNA "library"), by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U. K. Vol. I, II). Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Various strategies known in the art can be employed for cloning the auxiliary gene identified according to the invention, and the invention is not limited to any particular cloning strategy. In a preferred embodiment, the following basic strategy may be employed: (A) The Tn551 inactivated genes can be cloned in *E. coli*; (B) the cloned Tn551-carrying pieces of the chromosome can be used to find the active alleles in the parent bacterium, e.g., COL, chromosome; (C) the active alleles can be cloned into a shuttle-vector and assayed for the ability to complement, i.e., correct, the phenotype of the appropriate transposon mutant; and (D) the cloned gene, or genes can be sequenced. In a further aspect of the invention, this strategy can be implemented as follows:

(A) Cloning the insertionally inactivated (Tn551) form of auxiliary genes. 1. Digest the chromosomal DNA with different restriction enzymes, preferably selecting enzymes that cut once (or twice) inside Tn551, but that can be used for cloning in the plasmid to be used in the cloning, e.g., the pUC19 plasmid, or BLUESCRIPT. For example, the restriction endonuclease KpnI cuts Tn55I once and can be used with both vectors. The fragments are preferably separated by running in conventional electrophoresis. 2. Probe the fragments with the internal XbaI-HpaI fragment from Tn551 cloned into the plasmid pGEM-1 (plasmid pRT1, see Matthews and Tomasz, 1990, Antimicrob. Agents Chemother. 34:1777–79) to find positive fragments—there will be two if an enzyme that cuts Tn551 once is used. 3. Elute the appropriate fragment or fragments identified with the probe from the gel. 4. Ligate the fragment into an *E. coli* vector (e.g., pUC19) and transform using an appropriate strain of *E. coli* as the recipient. 5. Select transformed bacteria in plates containing X-gal and IPTG; colonies containing recombinant plasmids will be white under these conditions. 6. Select the white colonies containing the required chromosomal fragment by colony hybridization using a Tn551 probe, such as the XbaI-HpaI fragment. 7. Identify positive clones identified by probe hybridization and prepare plasmid DNA. 8. Check for the proper size insert in the plasmids. 9. Construct a physical map of the plasmid.

(B) Cloning of the active allele. 1. Prepare a probe from the plasmid carrying part of the Tn551 inactivated gene, i.e., vector+staphylococcus DNA insert+one end of Tn551. 2. Cut the chromosome of the parent strain, e.g., COL, with one of the enzymes used in cloning the fragment, which originates a Tn551-hybridizing fragment of approximately 10 kb. Probe with the plasmid fragment probe and find the positive band (corresponding to the active auxiliary gene. 3. Elute the band containing the chromosomal fragment identified with the probe, and ligate the eluted DNA into a shuttle vector, such as pGC2. 4. Transform *E. coli* by selecting for the intact plasmid vector marker AmpR. S. Probe transformants by colony hybridization, e.g., with the plasmid fragment probe. 6. Prepare plasmids and run on a gel. Identify the plasmids which are of larger size than the vector alone; these plasmids should have a size corresponding to the vector+insert. 7. Construct a physical map of the plasmid and compare it with the physical map of the plasmid containing the inactivated gene.

(C) Complementation assay. 1. The complementation assay involves the introduction of the recombinant plasmid putatively containing the inserted active allele of the auxiliary gene into the original aux mutant. The introduction of the recombinant vector can be attempted by electroporation (Luchansky et al., 1988, Mol. Microbio. 2:637–646), protoplast transformation (Chang and Cohen, 1979, Mol. Gen. Genet. 168:111–115), or prophage transformation (Pattee and Nevelin, 1975, J. Bacteriol. 124:201–211). The selection should be first for a plasmid marker, such as CmR (a plasmid pCG2 marker that is expressed in *S. aureus*), and then for methicillin resistance. If the complementation has worked fully, the phenotype of the transposon mutant carrying the shuttle vector with the aux gene should be the same as that of the original parent strain.

The step of cutting the chromosome of the parent strain can be simplified as follows: one class of mutants (located on the SmaI-A fragment) lie in the largest EcoRI fragment, of approximately 40 kb. This fragment can be easily resolved by PFGE electrophoresis from the other EcoRI fragments and eluted pure from the gel. The DNA of this 40 kb EcoRI fragment can then be cut with an appropriate restriction endonuclease as described in step B.2. The same simplification method can be applied to clone auxiliary genes that lie in the SmaI fragment I, and that lie in the largest HindIII fragment.

Generally, once the DNA fragments are generated, identification of the specific DNA fragment containing the desired auxiliary gene may be accomplished in a number of ways. For example, if an amount of a portion of an auxiliary gene or a fragment thereof is available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). Those DNA fragments with substantial homology to the probe will hybridize. The present invention provides specific examples of DNA fragments that can be used as hybridization probes for auxiliary genes, i.e., Tn551 mutants.

It is also possible to identify the appropriate fragment by restriction enzyme digestion(s) and comparison of fragment sizes with those expected according to a known restriction map if such is available. Further selection can be carried-out on the basis of the properties of the gene.

As described above, the presence of the gene may be detected by assays based on the physical, chemical, or immunological properties of its expressed product. For example DNA clones that produce a protein that, e.g., has similar or identical electrophoretic migration, isoelectric focusing behavior, proteolytic digestion maps, proteolytic activity, antigenic properties, or functional properties, especially cell wall synthetic activity, known for a particular auxiliary protein. In particular, DNA suspected of containing the auxiliary gene of interest can be introduced into a mutant bacterial strain, e.g., a strain corresponding to RUSA315, to reconstitute normal phenotypic methicillin resistance, cell wall synthesis, and the like.

Alternatives to isolating the auxiliary genomic DNA include, but are not limited to, chemically synthesizing the gene sequence itself from a known sequence. For example, DNA cloning of an auxiliary gene can be isolated from Gram positive bacteria by PCR. Other methods are possible and within the scope of the invention.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. For example, the auxiliary coding sequence can be inserted in an *E. coli* cloning vector. Other examples of vectors include, but are not limited to, bacteriophages such as lambda derivatives, or plasmids such as pBR322 derivatives or pUC plasmid derivatives, e.g., pGEX vectors, pmal-c, pFLAG, etc.

The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a "shot gun" approach. Enrichment for the desired gene, for example, by size fractionation, can be done before insertion into the cloning vector.

In specific embodiments, transformation of host cells with recombinant DNA molecules that incorporate the isolated auxiliary gene or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

The present invention also relates to vectors containing genes encoding analogs and derivatives of auxiliary proteins that have the same functional activity as an auxiliary proteins. The production and use of derivatives and analogs related to an auxiliary protein are within the scope of the present invention. In a specific embodiment, the derivative or analog is functionally active, i.e., capable of exhibiting one or more functional activities associated with a full-length, wild-type auxiliary protein.

In particular, derivatives can be made by altering encoding nucleic acid sequences by substitutions, additions or deletions that provide for functionally equivalent molecules. Due to the degeneracy of nucleotide coding sequences, other DNA sequences which encode substantially the same amino acid sequence as an auxiliary gene may be used in the practice of the present invention. These include but are not limited to nucleotide sequences comprising all or portions of auxiliary genes that are altered by the substitution of different codons that encode the same amino acid residue within the sequence, thus producing a silent change. Likewise, the derivatives of the invention include, but are not limited to, those containing, as a primary amino acid sequence, all or part of the amino acid sequence of an auxiliary protein including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

The genes encoding auxiliary protein derivatives and analogs of the invention can be produced by various methods known in the art. The manipulations which result in their production can occur at the gene or protein level. For example, a cloned auxiliary gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of an auxiliary protein, care should be taken to ensure that the modified gene remains within the same translational reading frame as the auxiliary gene, uninterrupted by translational stop signals, in the gene region where the desired activity is encoded.

Additionally, the auxiliary gene nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479–488; Oliphant et al., 1986, Gene 44:177; Hutchinson et al., 1986, Proc. Natl. Acad. Sci. U.S.A. 83:710), use of TAB® linkers (Pharmacia), etc. PCR techniques are preferred for site directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61–70).

Once the gene is cloned, its sequence can be determined using any of the sequencing techniques known in the art.

Moreover, if desired, the gene can be expressed recombinantly, using the well known techniques for recombinant gene expression, in order to obtain a large sample of purified protein for structural and functional studies.

The gene coding for an auxiliary protein, or a functionally active fragment or other derivative thereof, can be inserted into an appropriate expression vector, i.e., a vector which contains the necessary elements for the transcription and translation of the inserted protein-coding sequence. An expression vector also preferably includes a replication origin. The necessary transcriptional and translational signals can also be supplied by the native auxiliary gene and/or its flanking regions. A variety of host-vector systems may be utilized to express the protein-coding sequence. Preferably, however, a bacterial expression system is used to provide for high level expression of the protein with a higher probability of the native conformation. Potential host-vector systems include but are not limited to bacteria transformed with bacteriophage, DNA, plasmid DNA, or cosmid DNA.

The expression elements of vectors vary in their strengths and specificities. Depending on the host-vector system utilized, any one of a number of suitable transcription and translation elements may be used.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination).

Expression of nucleic acid sequence encoding an auxiliary protein or peptide fragment may be regulated by a second nucleic acid sequence so that the exported protein or peptide is expressed in a host transformed with the recombinant DNA molecule. For example, expression of an auxiliary protein may be controlled by any promoter/enhancer element known in the art, but these regulatory elements must be functional in the host selected for expression. For expression in bacteria, bacterial promoters are required ("Useful proteins from recombinant bacteria" in Scientific American, 1980, 242:74–94)

Expression vectors containing auxiliary gene inserts can be identified by four general approaches: (a) PCR amplification of the desired plasmid DNA or specific mRNA, (b) nucleic acid hybridization, (c) presence or absence of "marker" gene functions, and (d) expression of inserted sequences. In the first approach, the nucleic acids can be amplified by PCR with incorporation of radionucleotides or stained with ethidium bromide to provide for detection of the amplified product. In the second approach, the presence of a foreign gene inserted in an expression vector can be detected by nucleic acid hybridization using probes comprising sequences that are homologous to an inserted gene. In the third approach, the recombinant vector/host system can be identified and selected based upon the presence or absence of certain "marker" gene functions (e.g., β-galactosidase activity, PhoA activity, thymidine kinase activity, resistance to antibiotics, transformation phenotype, occlusion body formation in baculovirus, etc.) caused by the insertion of foreign genes in the vector. If the auxiliary gene is inserted within the marker gene sequence of the vector, recombinants containing the insert can be identified by the absence of the marker gene function. In the fourth approach, recombinant expression vectors can be identified by assaying for the activity of the gene product expressed by the recombinant. Such assays can be based, for example, on the physical or functional properties of the auxiliary gene product in suitable assay systems, e.g., cell wall synthesis.

Once a suitable host system and growth conditions are established, recombinant expression vectors can be propagated and prepared in quantity.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered auxiliary protein may be controlled. Furthermore, different host cells have characteristic and specific mechanisms for the translational and post-translational processing and modification (e.g., cleavage of signal sequence) of proteins. Appropriate cell lines or host systems can be chosen to ensure the desired modification and processing of the foreign protein expressed. Different vector/host expression systems may effect processing reactions, such as proteolytic cleavages, to a different extent.

Biochemical Activity of Auxiliary Proteins

Generally, the invention provides for identification of a functional property of a protein produced by an auxiliary gene by comparing the homology of the deduced amino acid or nucleotide sequence to the amino acid sequence of a known protein, or the nucleotide sequence of the gene encoding the protein.

An important aspect of the invention is ability to characterize the biochemical activity of the protein encoded by the auxiliary gene, particularly the auxiliary genes of mutant RUSA315, by biochemical and phenotypic analysis. Information about the biochemical activity of the protein provides direction for identifying antagonists, as described below.

Transposon inactivation experiments indicate that the functioning of the mecA gene and auxiliary genes are both essential for the expression of high level methicillin resistance. Although not intending to be limited by any particular theory, a conceivable model would be as follows. As the B-lactam antibiotic level begins to increase in the environment of the bacteria, the antibiotic molecules penetrate the cell surface and inactivate (by covalent bond formation) the normal complement of the four staphylococcal PBPs which have relatively high affinities for the drug molecules. In vitro experiments indicate that within the methicillin concentration range of 5 to 10 mg/L, all four "normal" PBPs become fully acylated. One may assume that under these conditions, perhaps upon the generation of a cellular signal, the low affinity PBP2A takes over the task of cell wall synthesis. It was shown that in the highly resistant strain COL (methicillin MIC=1600 mg/L), addition of 5–10 mg/L methicillin to the medium resulted in a striking change in the composition of peptidoglycan (de Jonge and Tomasz, 1993, Antimicrobial. Agents and Chemotherapy, 37:342–6). In drug free medium, this bacterium produces a cell wall composed of a diverse family of over 35 muropeptide components, the majority (60%) of which are trimers or higher oligomers of muropeptides. When grown in the methicillin containing medium, this complex wall structure is replaced by a simple one in which the peptidoglycan is made up of essentially two components; the pentaglycyl monomer and its dimer, with only a very small amount of trimers and traces of higher oligomers. Bacteria continue to produce this simple peptidoglycan throughout a vast range of antibiotic concentrations in the medium for 5 mg/L (<0.1% of the MIC) up to 750 mg/L (½xthe MIC). The observations suggest that at the critical concentration of about 5 mg/L methicillin, a new cell wall synthetic machinery, presumably PBP2A, takes over. In this model, PBP2A is assumed to be a peculiar transpeptidase which can only link two monomers together, but is incapable of generating the highly crosslinked oligomers which are the characteristic products of the normal wall synthetic machinery (de Jonge and Tomasz, 1993 supra). It may be that blocks in the synthesis of "normal" muropeptides (i.e., inactivation of auxiliary genes) can cause such striking reductions in the effectiveness of this resistance mechanism (i.e., decrease in the MIC from 1600 to 3 mg methicillin per liter) in spite of the presence of large amounts of PBP2A because effective functioning of PBP2A also requires an abundant supply of structurally correct cell wall building blocks. The correct building blocks may successfully compete with the methicillin molecules for the active site of PBP2A. Muropeptides of "incorrect" structure (e.g., less than five glycine units in the crosslinking peptides, or lack of amidation of the glutamic residues) compete less effectively with the antibiotic molecule, which translates to a decrease in the methicillin MIC value (see FIGS. 1A and B).

The role of auxiliary proteins in cell wall synthesis can be indirectly evaluated by analyzing the composition of the cell wall.

Cell wall peptidoglycan can be prepared from parental strains and from mutants.

Figure 2:
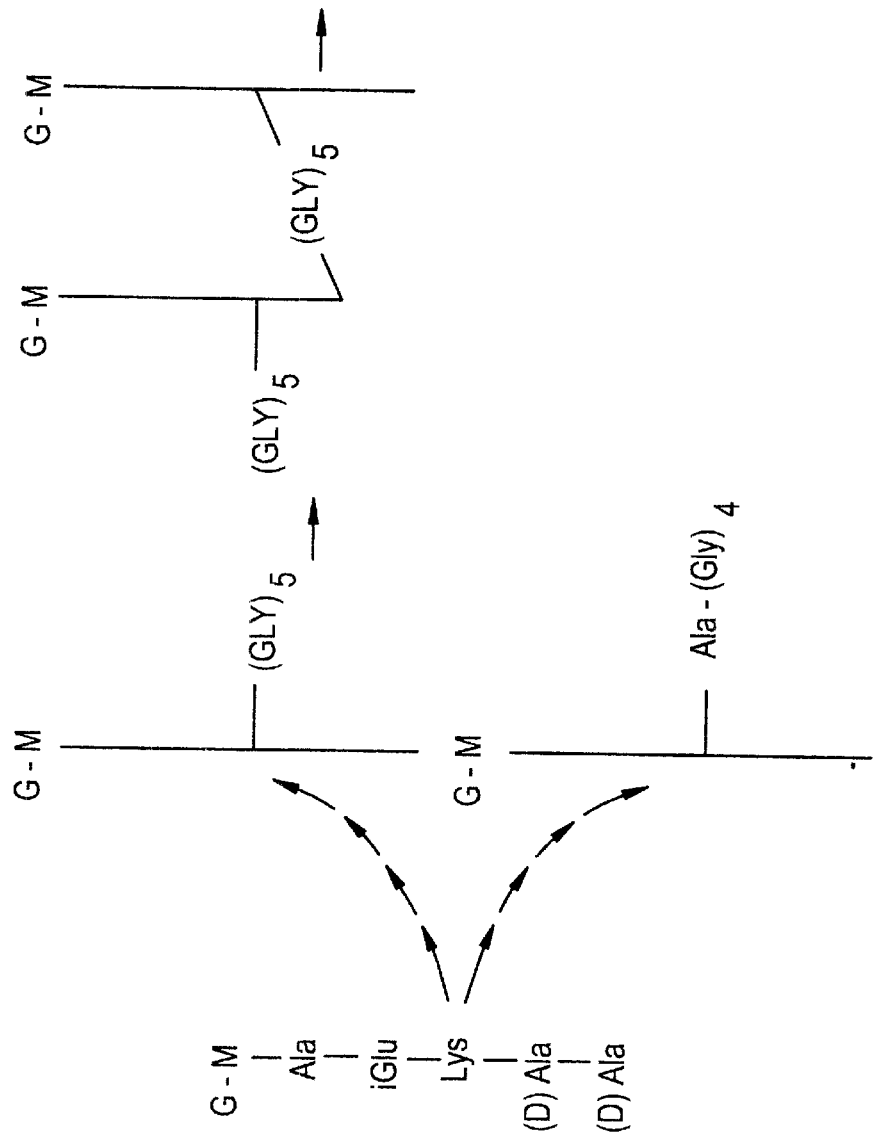
FIG. 2. (Prior Art) Suggested pathway for the addition of crosslinking peptides to the pentapeptide precursors. Symbols: G—N-acetylglucosamine; M—N-acetylmuramic acid; Ala, iGlu, Lys—alanine, isoglutamine and lysis, respectively. The synthetic pathway is interrupted at various steps in the auxiliary mutants. See WO 95/16039, supra.

The muropeptide building blocks of the peptidoglycan (liberated by enzymatic digestion) can be separated by reverse phase high performance liquid chromatography (HPLC) (de Jonge et al., 1992, J. Biol. Chem. 267: 11248–54). Inactivation of the mecA gene causes no detectable change in muropeptide composition. Inactivation of auxiliary genes may cause major and unique composition changes in the peptidoglycans, which can be identified by differences in HPLC elution profiles of muropeptides isolated from enzymatic cell wall peptidoglycan hydrolysates of a parental strain and of mutants (See e.g., de Jonge et al., J. Bacteriol. 173:1105–10; de Jonge et al., 1992, J. Biol. Chem. 269:11255–9; Maidhof et al., 1991, J. Bacteriol. 173:3507–13; de Jonge et al., 1993, J. Bacteriol. 175:2779–82). These unique wall composition changes may be reproduced with precision. The results can indicate, e.g., that auxiliary genes control the biosynthesis of the oligopeptide substituent on the epsilon amino group of the lysine residue in the muropeptide stem in staphylococci (FIG. 2). In the present invention, the auxiliary gene appears to regulate cell wall synthesis at or close to the branch point in hexose metabolism.

In another specific embodiment, based on the apparent similarity between the protein encoded by the gene identified in mutant strain RUSA315, which appears to encode a hexoseisomerase or a hexosamine isomerase, the biochemical effects will be manifested by a deficiency of hexose-derived cell wall compounds.

In parental strains COL and M100, the most abundant monomer is the disaccharide pentapeptide substituted with a pentaglycyl unit on the epsilon amino group of the lysine residue, and this monomer is also the major building block of dimers, trimers and higher oligomers of the peptidoglycan.

Various muropeptide alterations may be observed. For example, synthetic blocks can occur at a step past addition of a fourth glycine; at a step past the addition of a first glycine; in the synthesis of minor muropeptides; in the synthesis of peptidoglycans; or in the amidation of the x-carboxyl group of the stem peptide glutamic acid residues (see de Lencastre et al., 1994 "Molecular Aspects of Methicillin Resistance in *Staphylococcus aureus*", J. Antimicrob. Chemother. 33; de Jonge et al., 1992, J. Biol. Chem. 267:11255–9; Ornelas-Soares et al., 1993, J. Biol. Chem. 268:26268–72).

Auxiliary Gene and Protein Antagonists

Although bacterial mutation can be used to identify genes associated with antibiotic resistance, random mutagenesis to knock out auxiliary genes is not a therapeutically attractive treatment regimen for bacterial, in particular, staphylococcal, infection. Thus, the present invention contemplates inactivation of auxiliary genes and proteins, in particular the RUSA315 mutant gene and protein encoded thereby, using compounds that antagonize the activity of the protein, or with antisense nucleic acids to inhibit expression of the protein. For example, the activity for the protein encoded by the RUSA315 mutant gene may be related to that of hexoisomerase or hexosamine isolmerase because of its strong homology thereto. The latter enzyme is active close to a branch point in hexose metabolism where. specific cell wall compounds are beginning to be made.

In one embodiment, antisense nucleic acids that are complementary to the auxiliary gene mRNA can be administered to a subject suffering from a bacterial infection. Such nucleic acids can be DNA or RNA, preferably DNA, and more preferably DNA containing non-phosphate bonds, and thus is resistant to nuclease degradation in vivo.

As noted above, according to one non-binding theory of the invention, the suppression of antibiotic resistance by inactivation of these genes must be caused by the block in the production of the corresponding gene products that are essential for the phenotypic expression of resistance. Specific antagonists of these gene products can be screened for use as chemical agents capable of re-sensitizing the bacteria to beta lactam antibiotics.

One way for searching for such compounds would involve incorporating candidates into test systems containing appropriate concentrations of the beta lactam antibiotics and the test organisms, e.g., the highly methicillin resistant strain of *S. aureus*, strain COL. Effective compounds would be expected to reduce methicillin resistance at sub-inhibitory levels.

In another embodiment, screening for active compounds is based on observing similar or identical phenotypic changes in the antibiotic resistant bacteria, e.g., cell wall composition, accumulation of muramyl peptides, and the like, in the bacteria in the presence of a candidate inhibitor.

Identification and isolation of a gene encoding a FemR315 of the invention provides for expression of FemR315 in quantities greater than can be isolated from natural sources, or in indicator cells that are specially engineered to indicate the activity of FemR315 expressed after transfection or transformation of the cells. Accordingly, in addition to rational design of agonists and antagonists based on the structure of FemR315 polypeptide, the present invention contemplates an alternative method for identifying specific ligands of FemR315 using various screening assays known in the art.

Any screening technique known in the art can be used to screen for FemR315 agonists or antagonists. The present invention contemplates screens for small molecule ligands or ligand analogs and mimics, as well as screens for natural ligands that bind to and agonize or antagonize activates FemR315 in vivo. For example, natural products libraries can be screened using assays of the invention for molecules that agonize or antagonize FemR315 activity.

Knowledge of the primary sequence of the FemR315 protein, and the similarity of that sequence with proteins of known function, can provide an initial clue as the inhibitors or antagonists of the protein. Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" [Scott and Smith, 1990, *Science* 249:386–390 (1990); Cwirla, et al., *Proc. Natl. Acad. Sci.*, 87:6378–6382 (1990); Devlin et al., *Science*, 249:404–406 (1990)], very large libraries can be constructed ($10^6$–$10^8$ chemical entities). A second approach uses primarily chemical methods, of which the Geysen method [Geysen et al., *Molecular Immunology* 23:709–715 (1986); Geysen et al. *J. Immunologic Method* 102:259–274 (1987)] and the method of Fodor et al. [*Science* 251:767–773 (1991)] are examples. Furka et al. [14th *International Congress of Biochemistry*, Volume 5, Abstract FR:013 (1988); Furka, *Int. J. Peptide Protein Res.* 37:487–493 (1991)], Houghton [U.S. Pat. No. 4,631,211, issued December 1986] and Rutter et al. [U.S. Pat. No. 5,010,175, issued Apr. 23, 19911 describe methods to produce a mixture of peptides that can be tested as agonists or antagonists.

In another aspect, synthetic libraries (Needels et al., *Proc. Natl. Acad. Sci. USA* 90:10700–4 (1993); Ohlmeyer et al., *Proc. Natl. Acad. Sci. USA* 90:10922–10926 (1993); Lam et al., International Patent Publication No. WO 92/00252; Kocis et al., International Patent Publication No. WO 9428028, each of which is incorporated herein by reference in its entirety], and the like can be used to screen for FemR315 ligands according to the present invention.

The screening can be performed with recombinant cells that express the FemR315, or alternatively, using purified protein, e.g., produced recombinantly, as described above. For example, the ability of labeled, soluble or solubilized FemR315 that includes the ligand-binding portion of the molecule, to bind ligand can be used to screen libraries, as described in the foregoing references.

Knowledge of the primary sequence of the protein, and the similarity of that sequence with proteins of known function, can provide an initial clue as the inhibitors or antagonists of the protein. Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of inhibitors and antagonists.

Treatment of Antibiotic Resistant Bacterial Infections

The present invention provides methods and compositions for the treatment of infections with antibiotic resistant or multiple antibiotic resistant bacteria. In its primary aspect, the invention provides for co-administration of a compound that inhibits or antagonizes an auxiliary protein involved in cell wall synthesis in conjunction with an antibiotic or antibiotics to which the bacterium is normally resistant.

Accordingly, the invention provides pharmaceutical compositions comprising a compound that antagonizes an auxiliary protein in an amount effective to antagonize the activity of an auxiliary protein, and a pharmaceutically acceptable carrier. In another embodiment, the pharmaceutical composition further comprises an antibiotic in an amount effective to treat a bacterial infection.

Preferably, the antibiotic is any member of the beta lactam family of antibiotics. In a specific aspect, the antibiotic is methicillin.

A particularly attractive feature of this strategy is that it does not involve the search for new antibiotic agents but rather it proposes to find agents that bring the target bacterium back to within the inhibitory range of well characterized antibiotics such as beta lactams.

This strategy is also applicable for the selection of agents that could resensitize bacteria to other types of antibiotics also. In addition, agents capable of sensitization to methicillin may very well be active in a similar manner in beta lactam resistant strains of other bacterial species such as *Enterococcus faecium* and *E. faecalis*, penicillin resistant pneumococci ($pen^R$ pneumococci), and coagulase-negative staphylococci.

According to the present invention, the therapeutic compositions and methods of the invention can be used to protect an animal subject from infection of a Gram positive bacteria. Thus, a therapeutic composition or method of the invention can be used in birds, such as chickens, turkeys, and pets; and in mammals, preferably humans, as well as other mammalian species, including but not limited to domesticated animals (canine and feline), farm animals (bovine, ovine, equine, caprine, porcine, and the like), rodents, and undomesticated animals.

The present invention will be better understood from a review of the following illustrative description.

EXAMPLE 1

Molecular Cloning and DNA Sequencing a Phosphoglucomutase-Like Gene Essential for the Optimal Expression of Methicillin Resistance in *Staphytococcus aureas*

This Example describes the cloning and sequencing of a new auxiliary gene identified by Tn551 insertional mutagenesis of the highly and homogeneously methicillin resistant Staphylococcus aureaus strain COL. The insertionally inactivated mutant RUSA315 had intact mecA and normal amount of PBP2A, but drastically reduced antibiotic resistance (drop in methicillin MIC from 1600 $\mu$g $ml^{-1}$ to 1.5 $\mu$g $ml^{-1}$); a unique heterogenous phenotype; and a compositional change in the cell wall characterized by the complete disappearance of the unsubstituted disaccharide pentapeptide from the peptidoglycan. Cloning in *E. coli* followed by sequencing located the Tn551 insert Ω720 in an open reading frame of 451 codons, provisionally called femR315, defined a polypeptide with a deduced amino acid sequence that showed over 26% sequence identity and 51% overall sequence similarity with the phosphoglucomutase (PGM) gene of *E. coli*. The Tn551 insertion site of a previously described mutant 12F (femD) also lies in the same gene as femR315. The wild type form of femR315 subcloned in a shuttle vector fully restored expression of high level (parental) methicillin resistance in mutant RUSA315. Enzymes similar to PGM catalyze the isomerization of hexose and hexosamine phosphates leading to the formation of glucosamine-1-P, which is an obligate precursor in the biosynthesis of UDP-N-acetylglucosamine (UDP-NAGA). The suppression of the methicillin resistance of RUSA315 appears to be related to some functional or quantitative abnormality of UDP-NAGA metabolism.

Materials and Methods

Bacterial strains, phage and plasmids. The bacterial strains, phage and plasmids used in this study are described in Table 1.

TABLE 1

Strains, phages and plasmids in the this study

| Strain/phage/plasmid | Relevant characteristics | Origin of reference |
|---|---|---|
| Strain *Esherichia coli* | | |
| DH5α | recA1 gyrA96 thi-1 hsdR17 supE55relA1 Φ80 dlac ZΔ M15 | BRL |
| XL1-Blue MRA | Δ(MCRA) 183Δ (MCRCB-HSD SMR-mrr) 173endA1 supE44 thi-1 gyrA96 relA1 lac | Stratagene |
| XL1-Blue MRA(P2) | XL1-Blue MRA (P2 lysogen) | Stratagene |
| *Staphylococcus aureus* | | |
| RN4220 | Restriction | |
| COL | Homogeneous $Mc^r$ | RU collection |
| RUSA315 | COLΩ720 (femR315::Tn551) $Em^r$ heterogeneous $Mc^r$ | (1) |
| RUSA12F | COLΩ558 (femD::Tn551) $Em^r$ heterogeneous $Mc^r$ | (2), (3), (4) |
| SWET3 | Restriction $Amp^r$ $Cm^r$ (RN4220/pGCSW-3) | This study |
| SWTD3 | COLΩ720 (femR315::Tn551) $Em^r$ $Mc^r$ $Cm^r$(RUSA315/pGCSW-3) | This study |
| SWTD5 | COLΩ558 (femD::Tn551) $Em^r$ $Mc^r$ $Cm^r$(RUSA12F/pGCSW-3) | This study |
| Bacteriophage | | |
| Lambda DASH ®II | λsbhλ1° b189 KH54 chiC srIλ4° nin5 shndIIIλ6° srIλ5° $red^+$ $gam^+$ | Stratagene |
| λDII/R315 | Lambda DASH ®II/15.5 kb EcoR1 fragment from RUSA315(femR315::Tn551) | This study |
| λDII/COL-R315 | Lambda DASH ®II/10.3 kb EcoR1 fragment from RUSA315(femR315 wild-type) | This study |
| Plasmid | | |
| pGEM-3Z | Subcloning vector $Amp^r$ | Promega Corp. |
| pRT1 | pGEM-1/4.0 kb Xba-Hpa1 fragment of Tn551 | (5) |
| pSW-4 | pGEM-3Z/5.0 kb Pst1 fragment from λDII/COL-R315 (femR315 wild-type) | This study |
| pSW-4A | PGEM-3Z/2.2 kb Pst1-EcoRV fragment from pSW-4 (femR315 wild-type) | This study |
| pSW-8 | pGEM-3Z/2.7 kb KpnI-BamHI fragment from λDII/R315 (Tn551/JL::femR315 flanking) | This study |
| pGC2 | Shuttle vector $Amp^r$ $Cm^r$ | |
| pGCSW-3 | pGC2/2.2 kb Pst1-EcoR1 fragment from pSW-4A (femR315 wild-type) | This study |

$Mc^r$, methicillin resistance; $Em^r$, erythromycin resistance; $Amp^r$, ampicillin resistance; $Cm^r$, chloramphenicol resistance
References:
(1) de Lencastre and Tomasz, Antimicrob. Agents Chemother., 38:2590 (1994);

TABLE 1-continued

Strains, phages and plasmids in the this study

| Strain/phage/plasmid | Relevant characteristics | Origin of reference |
|---|---|---|

(2) Korblum et al., Eur. J. Clin. Microbiol., 5:714–718 (1986);
(3) Berger-Bächi et al., Antimicrob. Agents Chemother., 36:1367–1373 (1992);
(4) de Lencastre et al., J. Antimicrob. Chemother., 33:7–24 (1994);
(5) Matthews and Tomasz, Antimicrob. Agents Chemother., 34:1777–1779.

Media and growth conditions. *Staphylococcus aureus* and MRSA mutants were grown as described before [Oshida and Tomasz, *J. Bacteriol.*, 174:4952–4959 (1992)]. Luria-Bertani (LB) medium was used to propagate *Esherichia coli* DH5a, and ampicillin was added at the concentration of 100 µg/ml for selection and maintenance of the plasmids listed in Table 1. *Esherichia coli* XL1-blue MRA and MRA(P2) were the host cells for Lambda DASH®II phage. They were cultured as recommended by the supplier (Stratagene Cloning Systems, La Jolla, Calif.).

Susceptibility testing and population analysis. One colony of bacterial strain was inoculated into 5 ml of TSB (tryptic soy broth, Difco Laboratories) and incubated at 37° C. with 200 rpm rotation for overnight. Culture density ($OD_{600}$) was adjusted to give a viable titer of $10^8$ to $10^9$ cfu/ml. Sterile swabs were dipped into the bacterial suspension and applied to TSA (tryptic soy agar, Difco Laboratories) plates without antibiotics, and 6-mm-diameter disks containing antibiotics were applied to the plates with a disk dispenser (BBL, Beckton-Dickinson and Company). The antibiotics used were as follows: 1 mg of methicillin, 10 U of penicillin, 30 µg of cefazolin, 20 µg of ampicillin/sulbactam, 15 µg of erythromycin, 10 µg of gentamicin, 30 µg of tetracycline, 30 µg chloramphenicol, 5 µg of rifampin, and 5 µg of ciproflaxin (BBL, Becton Dickinson and Company). Diameters of inhibition zones were read after incubation at 37° C. for 24 h. To perform population analysis, aliquots of overnight cultures were spread onto TSA plates containing increasing concentrations of methicillin. CFU were determined after 48 h of incubation at 37° C. [de Lencastre et al., *Antimicrob Agents Chemother.* 35:632–639 (1991)].

DNA methods. All routine DNA manipulations were essentially performed as in Sambrook [Sambrook et al., *Molecular Cloning: a laboratory manual*, Cold Spring Harbor Laboratory, N.Y. (1989)] and Ausubel [Ausubel et al., *Short protocols in molecular biology*, Green Publishing Associates and John Wiley and Sons, NY (1992)]. Restriction enzymes, calf intestine alkaline phosphatase and T4 DNA ligase were purchased from New England Biolabs, Inc. and used as recommended by the manufacturer. Southern analysis was performed with ECL™ random prime labelling and detection systems purchased from Amersham Life Science according to the recommendation of the manufacturer.

Transformation of *S. aureus* by electroporation. *S. aureus* RN4220 (r-) was used as the primary recipient for recombinant pGC2 shuttle plasmids. The cells were harvested in mid-exponential growth (OD 578=0.5–0.55), washed with ½ volume of electroporation buffer (2.5 mM sodium phosphate buffer pH 7.4, 272 mM sucrose, 1 mM MgCl), and then resuspended in 1/300 volume of electroporation buffer. Forty µl of the cell suspension was incubated with 0.1 µg plasmid DNA for 30 min at room temperature. A pulse of 25 µF, 2 kV and 200 ohm was delivered by the Gene Pulser (BioRad). The cells were then transferred to 960 µl of LB and incubated at 37° C. for 1 h before plating aliquots on selective plates containing 10 µg/ml chloramphenicol. The shuttle plasmids were subsequently transduced from the electro-transformant by phage 80 α to the appropriate recipient strain, as described [Oshida and Tomasz, 1992, supra].

DIVA sequence analysis. Double-stranded DNA sequencing was accomplished by the dideoxy chain termination method [Sambrook et al., 1989, supra] with templates of DNA fragments cloned in pGEM-3Z. The oligonucleotide perimeters were synthesized and purified by Genosys Biotechnologies, Inc. Sequenase 2.0 (United States Biochemicals) was employed for chain elongation, and [$^{35}$S]-dATP-labelled samples were run in 8M urea/6% polycrylaminde gels. Nucleotide and derived amino acid sequences were analyzed with the Wisconsin Genetic Computer Group (GCG) software.

PCR. PCRs were carried out to detect the relation between the insertion site Ω558 in RUSA12F and Ω720 in RUSA315. Three oligonucleotide primers were ORF45 IN specific for the DNA sequence of FemR315 N-terminal (5-GGAAATATIIIGGTACAG-3')(SEQ ID NO:8), Tn551JROUT specific for a partial DNA sequence of Tn551 right junction (5'-TATTATCTATTCCTAAACAC-3')(SEQ ID NO:9), and Tn551JLOUT specific for a partial DNA sequence of Tn551 left junction (5'-GATGTCACCGTCAAGTFA-3')(SEQ ID NO:10). The chromosomal DNAs of RUSA315 and RUSA12F were prepared as templates. PCR amplification was performed in a DNA thermal cycler (Perkin-Elmer Cetus) by using PCR reagent kit (Perkin-Elmer Cetus) according to the manufacture. Thirty cycles were used for each reaction, with the following temperature profiles: 94° C., 5 min; 30×[92° C., 1 min; 40° C., 1 min; 72° C., 1 min], 4° C., hold.

Procedures used for sequence and structure database searching to find the relation to PGM were described by Sali [Sali and Blundell, *J. Mol. Biol.*, 234:779–815 (1993); Sali et al., Proteins, (1995)].

Results

Figure 3:
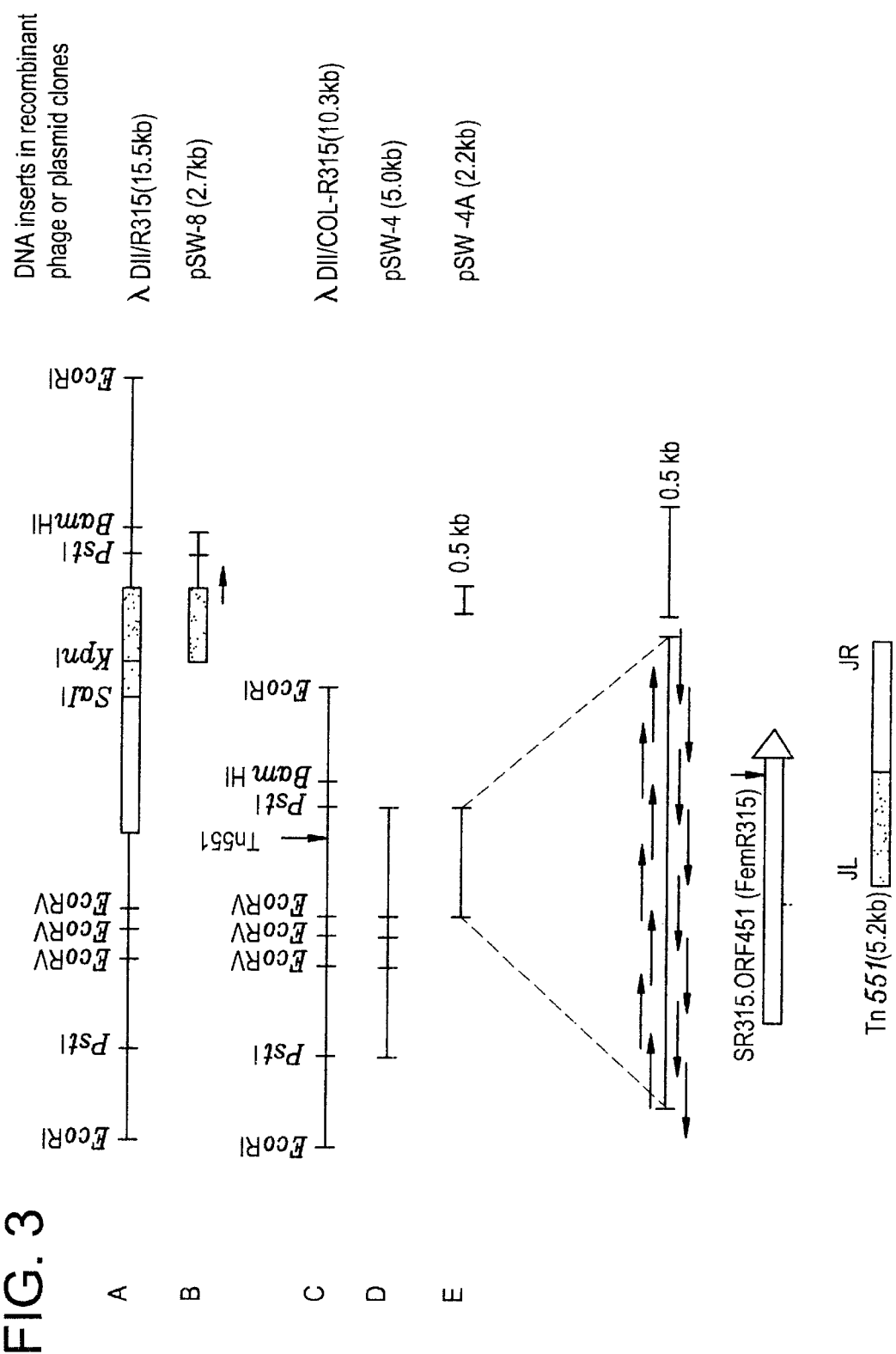
FIG. 3. Restriction map, genetic organization and sequencing strategy of the femR315 region. (A) Restriction map of 15.5 kb DNA insert in λDII/R315, transposen Tn551 is shown as box. (B) 2.7 kb DNA insert in pSW-8, box is the Tn551 left junction and the arrow is the direction of sequencing. (C) Restriction map of 10.3 kb DNA insert in λDII/COL-R315, Tn551 insertion site of Ω720 is shown. (D) 5.0 kb DNA insert in pSW-4. (E) 2.2 kb DNA insert in pSW-4A, the small arrows indicate the sequencing strategy, and the open reading frame of fem315 is shown as a box with a triangle to indicate the orientation of this ORF.

Cloning of Ω720 (femR315:Tn551). The insertion site 0720 of transposon Tn551, which generated the insertional mutant RUSA315, is located on a 10.3 kb EcoRt DNA fragment of the COL chromosome [DeLencastre and Tomasz, *Antimicrob. Agents Chemother*, 38:2590–2598 (1994)]. The approximately 15.5 kb EcoR1 fragment (which includes transposon Tn551) was isolated from strain RUSA315 and was ligated with the lambda DASH®II/EcoRI phage vector. An internal DNA fragment of Tn551 was purified from plasmid pRT1 and labeled with ECL™ random prime labelling and detection system as probe to screen the EcoRI sublibrary of RUSA315 in the lambda phage vector. The recombinant λ phage was named λDII/R315, and physical mapping of the DNA insert was obtained by digestion with various restriction endonucleases and Southern hybridization (FIG. 3A). The PstI, EcoRV, and BamHI recognition sites on the flanking sequence of Tn551 were mapped with respect to the unique SalI restriction site of Tn551. This physical mapping showed that the Tn551 insertion site Ω720 in mutant RUSA315 is located in a 2.2 kb EcoRV-PstI segment, which was included in the 5.0 kb PstI fragment, and that the end of Tn551 left junction is about 1.2 kb from the BamHI restriction site. The 2.7 kb KpnI-BamHI fragment which includes 1.5 kb of the left junction of Tn551 plus 1.2 kb of flanking sequence was isolated from the DNA of λDII/R315 and ligated to KpnI/BamHI-digested pGEM-3Z to form the recombinant plasmid pSW-8 (FIG. 3B).

Figure 4:
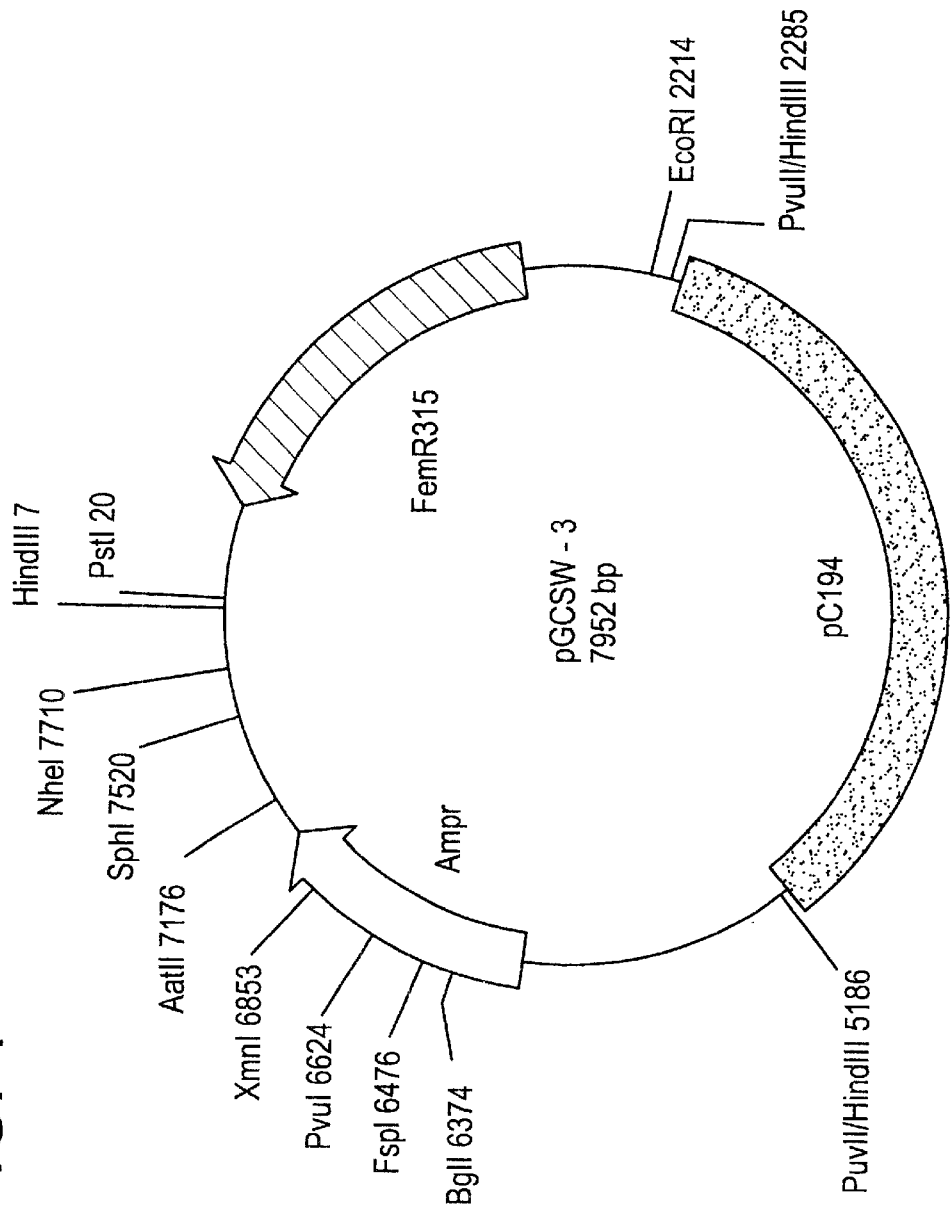
FIG. 4. Physical map of plasmid pGCSW-3. The shuttle plasmid pGC2 was constructed by inserting the plasmid pC194 into the PvuII site of pGEM-1 [Matthews and Tomasz, *Antimicrob. Agents Chemother.*, 34:1777–79 (1990)]. The 2.2 kb insert fragment of pSW-4A was subcloned into EcoRi/PsI sites of pGC2.

Cloning of the RUSA315 wild-type allele. An EcoRI sublibrary of the highly methicillin resistant parental strain COL was constructed in λ phage by ligating the approximately 10 kb EcoRI DNA fragment of COL chromosome with λDASH®II/EcoRI phage vector. The recombinant λ phage carrying the RUSA315 wild-type allele was identified by screening this EcoRI library with the ECL-labeled 2.7 kb Kpn[-BamHI fragment of pSW-8 and was named λDII/COL-R315. The 5.0 kb PstI fragment of λDII/COL-R315 (FIG. 3C) was isolated and ligated with PstI-digested pGEM-3Z to give a recombinant plasmid pSW-4 (FIG. 3D). Next, the plasmid pSW-4 was digested with EcoRV and SmaI, and then the 4.9 kb fragment of pSW-4 was purified and self-ligated by using the SmaI and EcoRV restriction sites of this fragment in order to generate plasmid pSW-4A (FIG. 3E). Plasmid pSW-4A contains the 2.2 kb insert of λDII/COL-R315 covering the Ω720 insertion site: thus the region of femR315 wild-type allele was cloned. From pSW-4A, the 2.2 kb insert fragment extending from the PstI site to the EcoRI site of the polyliner of pGEM-3Z was subconed into shuttle vector pGC2 yielding recombinant shuttle plasmid p(CSW-3 (FIG. 4).

Figure 5:
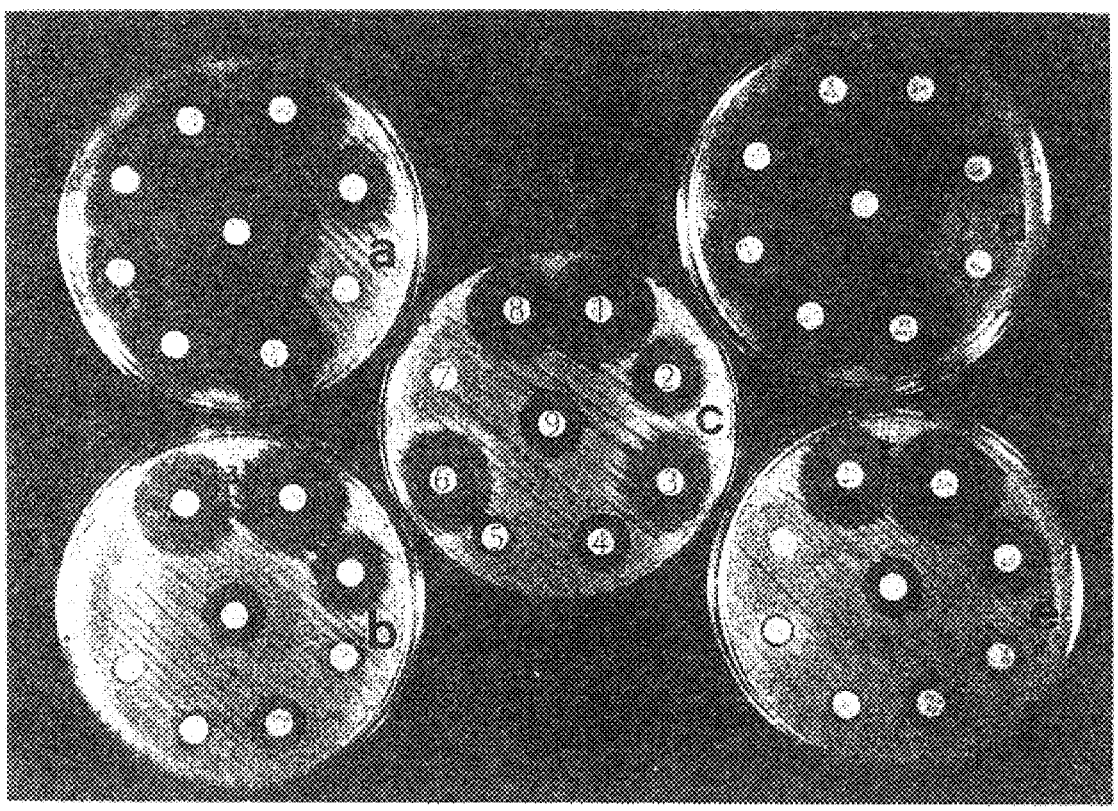
FIG. 5. Antimicrobial susceptibility of various strains. The standard disk susceptibility procedure was used to test the antimicrobial susceptibility of RUSA315 (plate a), SWTD3 (plate b), COL (plate c), RUSA 12F (plate d), SWTD5 (plate e). Antibiotics: 1, rifampin; 2, gentamicin; 3, erythromycin; 4, ampicillin/sulbactan; 5, penicillin; 6, chloramphenicol; 7, cefazolin; 8, ciprofloxin; 9, methicillin.

Complementation analysis with plasmid pGCSW-3. Plasmid pGCSW-3 was transformed into *S. aureus* RN4220 (r-) by electroporation and the electro-transformant SWET3 was used as donor to introduce pGCSW-3 into recipients RUSA315 and RUSA12F. The transductants SWTD3 and SWTD5 showed restored resistance to methicillin, penicillin, cefazoline and ampicillinisulbactam (FIG. 5). Population analysis indicated that this transductant SWTD3 expressed the same level of methicillin resistance as the parental $Mc^r$ strain COL (data not shown).

DNA sequence of the femR315 region. The 2187 basepair (bp) DNA insert depicted in FIG. 6 was sequenced through both strands with the strategy of primer walking. The sequencing of pSW-4A DNA insert was initiated with vector-based pUC/M13 forward at the EcoRV end and pUC/M13 reverse at the PstI end. Twelve more oligonucleotide primers were subsequently synthesized as new sequences were identified in order to generate enough overlapping region in the process of primer walking. The 2187 bp region was analyzed for open reading frames (ORFs). An ORF of 451 codons was found encoded by the strand extending from the EcoRV to the PstI site. This ORF, designated as FemR315, begins with the characteristic ATG initiation codon and ends with a TAA termination codon. The FemR315 is preceded by sites similar to the *Escherichia coli* consensus ribosome-binding sequence [Shine and Dalgarno, *Proc. Natl. Acad. Sci. USA*, 71:1342–1343 (1974)], which is 7 nucleotides upstream of the FemR315 initiation codon. A putative promoter sequence (Rosenberg and Court, *Ann. Rev. Genet.*, 13:319–353 (1979)], TTATA for the −35 region and TAAATT for the −10 region, was found 3 nucleotides upstream of the Shine-Dalgarno sequence. In addition, two palindromic sequences were also identified. The first one is located 68 bp upstream from the putative −35 region of FemR315 and includes the sequence from 290 to 328 bp which is able to form a structure with a stem of 14 bp and loop of 8 bp located 42 nucleotides downstream from the termination codon of FemR315. No ORF of significant length was found on the reverse complement of the sequence.

To determine the Tn551 insertion site Ω720 in mutant RUSA315, the DNA insert of pSW-8 was also partially sequenced initiated with an oligonucleotide primer based on the left junction of Tn551 (FIG. 3B). The sequence generated includes about 50 bp of the Tn551 left junction and 300 bp of flanking region. By matching the sequence of pSW08 and that of pSW-4A, the insertion site of Ω720 was determined to be between 1521 and 1522 bp, which is 1077 bp from the initiation codon and 272 bp from the termination codon of FemR315.

Detection of the Tn551 insertion site Ω558 in mutant RUSA12F by PCR. A 1.2 kb amplification product was obtained when PCR was performed by pairing the primer ORF451N with the primer Tn551JROUT and using RUSA315 chromosomal DNA as template. When the RUSA12F chromosomal DNA was employed as template, the primer pair of ORF451N and Tn555JROUT yielded no PCR product; however, a 1.15 kb PCR product was amplified by using primer ORF451N and Tn55JLOUT. The result indicated that the Tn551 insertion site of 558 in RUSA12F is located approximately 50 bp upstream from that of Ω720 in RUSA315, but the orientation of transposon Tn551 in these two mutants is reversed. RUSA315 and mutant 12F [Kornblum et al., *Eur. J. Clin. Microbiol.*, 5:714–718 (1986)] represent two different insertional mutants in the same gene formerly called femD.

Comparison of the amino acid sequence of FemR315 with known proteins. The deduced amino acid sequence (FIG. 6) of Fem315 was compared with sequences of known polypeptides in both Tblasn and Blastp databank (1994). Using the appropriate search programs [Sali and Blundell, 1993, supra; Sali et al., 1995, supra], the amino acid sequence of FemR315 showed significant homology with proteins of *Mycobacterium leprae* UreD, *Helicobacter pylori* UreC, *Escherichia coli* PGM, *Pseudomonas aeruginosa* phosphomannonmutase (PMM), and rabbit muscle PGM (Table 2).

TABLE 2

Amino acid sequence similarity of FemR315 with known proteins

| Organism | Protein | No. of aa | % Similarity |
|---|---|---|---|
| *Mycobacterium leprae* | UreD | 462 | 65 |
| *Helicobacter pylori* | UreC | 444 | 61 |
| *Escherichia coli* | PGM | 455 | 57 |
| *Pseudomonas aeruginosa* | PMM | 462 | 53 |
| Rabbit muscle | PGM | 561 | 51 | aa, amino acid; Ure, urease; PGM, phosphoglucomutase; PMM, phosphomannomutase

A multiple amino acid sequence alignment of FemR315, *Mycobacterium leprae* UreD (MiUreD), *Helicobacter pylori* UreC (HpUreC), *Escherichia coli* PGM (EcoPGM) and *Pseudomonas aeruginosa* PMM (PaPMM) with rabbit muscle PGM(RmPGM) was prepared by Modeller [Sali and Blundell, 1993, supra]. It was then inspected to better understand the significance of the overall similarities among the amino acid sequences (FIG. 7). While enzymatic properties of *Escherichia coli* PGM and *Pseudomonas aeruginosa* PMM have been described [Pradet and Boquet, Res. Microbiol., 142:37–45 (1991); Sá-Correia et al., *J. Bacteriol.* 169:3224–3231 (1987); Zelinski et al., *J. Biol. Chem.* 266:9754–9763 (1991)], RmPGM was chosen as the reference in the multiple amino acid sequence alignment analysis because the biological function has been characterized by kinetic studies [Rhyu et al., *Bio chem.*, 24:4746–4753 (1985);. Zielinski et al., 1991, supra] and because its three-dimensional structure has been determined by x-ray crystallography [Dai et al., *J. Biol. Chem.*, 267:6322–6337 (1992)]. Using this analysis, sequence patterns believed to be critical for the enzymatic activity of RmPGM [Dai et al., 1992, supra; Ray et al., *J. Biol. Chem.* 258:9166–9174

(1983)] were identified within the amino acid sequence of FemR315, HpUreC, M1UreD, EcoPGM, PaPMM and RmPGM sequences (FIG. 7). Such patterns include the substrate binding and catalysis region (RmPGM positions 115–119, FIG. 7, box a); the metal-binding loop (positions 286–292, FIG. 7, box c), and other three active site flaps (positions 258–262, FIG. 7, box b; 374–377, FIG. 7, box d; 388–392, FIG. 7, box e).

A more detailed comparison of FemR3 15 and RmPGM in the key regions of amino acid sequences is presented in FIG. 8. The amino acid sequence Thr-Ala-Ser-His-Asn (RmPGM positions 114–119 FIG. 8A)(SEQ ID NO:11) is known to be critical for PGM activity; the sequence is within the 21 amino acid long active site region of PGM [Ray et al., 1983, supra]. A similar amino acid sequence Ser-Ala-Ser-His-Asn (SEQ ID NO:12) was found in the femR315 coding sequence (FemR315 positions 100–105, FIG. 8A). The region surrounding the Ser-Ala-Ser-His-Asn sequence in FemR315 was compared with the 21 amino acid long active site region of RmPGM (FIG. 8A). Considerable degree of homology (62%) was observed between FemR315 and RmPGM in this region (which lies in the N-terminal portion of both protein). Furthermore, of the matched amino acids comprising this 62% homology, 69% (9 out of 13) were exact matches (FIG. 8A). The sequences of the metal ion binding loop (-Asp-$^{287}$-Gly$^{288}$-Asp$^{289}$-Gly$^{290}$-Asp$^{291}$-) (SEQ ID NO:13) and its two anchoring residues (Phe$^{286}$ and Arg$^{292}$) in RmPGM were also identical to a segment in FemR315 (positions 241–247, FIG. 8C). Three other short polypeptide chains (representing flaps of the active-site cleft of rabbit muscle PGM [6]), which includes His$^{260}$, Ser$^{377}$ and Lys388 respectively, also exhibited close similarities between RmPGM and FemR315 (FIGS. 8B, 8D, 8E).

Discussion

Identity of ORF femR315 and femD. The Tn551 insert Ω720 was shown to reduce the methicillin MIC (μg/ml) of the parental strain from 1600 μg ml$^{-1}$ to 1.5 μg ml$^{-1}$, and also generated a heterogenous phenotype. The insertion site of Ω720, together with at least five additional independent inserts (Ω721, Ω722, Ω723, Ω724, and Ω725), was located on the SmaI-I fragment, at a site that appears to be a hot spot for Tn551 insertion, and was mapped to share the same restriction pattern with HindIII, EcoRI, EcoRV, and PstI. The RUSA315 cluster maps in the same EcoRI, EcoRV, and PstI fragments the one of RUSA12F [DeLencastre and Tomasz, 1994, supra], but has a different HindIII restriction pattern from the one of the RUSA12F. The compositional change of peptidoglycan in RUSA315 was the complete disappearance of the unsubstituted disaccharide pentapeptide monomer, which was identical to that in RUSA12F [DeJonge et al., J. Biol. Chem., 267:11255–11259 (1992)]. To facilitate discussion, the putative genetic determinant inactivated by Tn551 insertion in the femD-type mutant RUSA315 was provisionally named,as femR315.

The insertion site of Ω720 was identified in the new auxiliary mutant femR315 through cloning and sequencing as an in-frame insertion of Tn551 that interrupts transcription of this ORF or causes abnormal transcription to yield a gene product with reduced activity. This in-frame mutation of femR315 appears to be directly or indirectly responsible for generating the reduced and heterogeneous antibiotic resistance phenotype and the change in peptidoglycan composition of mutant RUSA315.

Introduction of the shuttle plasmid pGCSW-3, which contains the intact femR315 into RUSA315 and RUSA12F, resulted in the full restoration of high-level resistance in both of these mutants, and these complementation experiments provided the evidence that the cloned pgm-like gene of femR315 was indeed the 20 genetic element responsible for the phenotype changes in both RUSA315 and RUSA12F. The insertion site of Ω558 was determined by PCR to be in the same ORF as that of Ω720, thereby confirming that the so-called femD is actually the identical gene characterized here as femR315.

The biochemical nature of femR315: sequencing similarities to determinants of PGM-like enzymes. The biochemical functions of staphylococcal auxiliary genes which have been identified so far are not fully understood. While femA and femB are clearly involved with the structure of crosslinks in the cell wall muropeptides, it is not yet clear whether these are structural genes for enzymes catalyzing the addition of amino acid residues to the chain of crosslinking oligopeptides or genes in some related regulatory function.

The amino acid sequence similarity between the several regions that are important for enzymatic activity of rabbit muscle PGM, Escherichia coli PGM, Pseudomonas aeruginosa PMM, and the corresponding regions of FemR315 (FIG. 7) suggests that the gene product of femR315 may perform in S. aureaus a catalytic function similar to that of PGM or PMM. Both PGM and PMM can catalyze internal transfer of phosphate residues on a hexose molecule from one hydroxyl group to another [Rhyu et al., 1985, supra; Zielinski et al., 1991, supra]. PGM catalyzes the interconversion of glucose-6-phosphate (G6P) and glucoze-1-phosphate (G1P) in various organisms, and the G1P serves as a substrate for the UDP-glucose pyrophospharylase-catalyzed condensation with UTP to form UDP-glucose, which is a common nucleotide sugar involved in synthesis of glycoproteins. In the peptidoglycan biosynthesis of Staphylococcus aureaus, the first step in the formation of nucleotide-linked cell wall precursors is the reactions of N-acetylglucosamine-1-phosphate (GlcNAc-1-P) with UTP, catalyzed by UDP-N-acetylglucosamine pyrophosphorylase, to yield UDP-N-acetylglucosamine (UDP-GlcNAc), a reaction analogous with the reactions that lead to the production of UDP-glucose and other UDP-linked sugars. UDP-GlcNAc is not only the precursor of UDP-N-acetylmuramic acid, but is also the source of the GlcNAc residue as it is transferred to undecaprenyl-PP-N-acetylmuramyl pentapeptide. If the gene product of femR315 is assumed to have a PGM-like enzyme activity, it may catalyze the conversion of GlcNAc-6-P to GlcNAc-1-P, the latter being a key intermediate in cell wall biosynthesis since it is the substrate of the UDP-N-acetylglucosamine pyrophosphorylase catalyzed reaction yielding UDP NAGA [Ghuysen and Shockman, Bacterial membranes and Walls, Marcel Dekker: New York pp. 37–130 (1973)]. While a specific bacterial isomerase of this type has not yet been described, PGM are known to be capable of catalyzing interconversion of 1–6 and 6-phosphate isomers of many alpha-D-hexoses as well as those of GlcNAc [Ray and Peck, The Enzymes, vol. 6, Academic Press: New York pp. 407–477 (1972)]. A partial defect in a PGM-like enzyme may affect the methicillin resistant phenotype and cell wall composition in the following manner. The absence of the unsubstituted disaccharide pentapeptide monomer from the peptidoglycan of mutant RUSA315 may be the consequence of a slow-down in the production of the murarmyl pentapeptide due to the partial block of GlcNac-1-P synthesis which, in turn, would limit availability of UDP NAGA for peptidoglycan synthesis. It has been proposed that in vivo, bactoprenyl-linked cell wall precursors may compete with the methicillin molecule for some site on PBP2A and an abnormality of chemical structure in the wall precursors (as in the case of femA, FemB, and femc mutants) tilts the balance of this competition in favor of the antibiotic resulting in reduced MIC value [DeLencastre and Tomasz, 1994, supra]. In the case of RUSA315, a quantitative reduction in the pool size of the wall precursors may favor interaction of PBP2A with the antibiotic, causing decrease in the MIC value.

The femR315 gene product. The gene product of femR315 appears to be PGM or an enzyme specific to the isomerization of GlcNac. The GlcNac phosphates are much less reactive with PGM than glucose phosphates [Ray and Peck, 1972, supra]. If the gene products of femR315 were the PGM of *Staphylococcus aureus*, then one may expect that the insertional mutant RUSA315 would exhibit pleiotrophic properties related to the perturbation of any one or several of the metabolic events catalyzed by this enzyme in the cell.

Alternatively, femR315 may be the structural gene of an enzyme the catalytic activity of which would be specific for isomerization of GlcNac phosphates. A complete inhibition of this enzyme in RUSA315 may then necessitate the take-over of the function of this enzyme by phosphoglucomutase, an enzyme with relatively poor efficacy in the catalysis of the isomerization of hexosamine phosphates. The resulting slow-down of this enzymatic step may then lead to the defective phenotype of RUSA315.

These proposals are based on DNA sequence comparison. Unambiguous assignment of function to the femR315 gene is now possible by isolation of its gene product and identification of its enzymatic function(s).

Interpretation of sequence similarities to UreD and UreC. The amino acid sequence of FemR315 also exhibited a high degree of similarity with UreD of *Mycobacterium leprae* and UreC of *Helicobacter pylori* (Table 2). *Mycobacterium leprae* UreD is one of the ORFs in a hypothetical urease operon on the chromosome of *Mycobacterium leprae* [Rinke de Wit et al., Mol. Microbiol., 6:1995–2007 (1992)]. The function of the gene product encoded by this operon has not been investigated. *Helicobacter pylori* UreC is one of the accessory factors in urease gene cluster, and was supposed to play a regulatory role for the expression of urease because deletion of both UreC and UreD regions resulted in the increase of urease activity [Cussac et al., *J. Bacteriol.* 174:2466–2473 (1992); Labigne et al., *J. Bacteriol*, 173:1920–1931 (1991)]. However, the effect of *Helico- bacter pylori* UreC gene itself on urease activity has not been investigated. Urease, which catalyzes the hydrolysis of urea to ammonia and carbon dioxide, is found in many species of plants, bacteria, and fungi [Mobley and Hausinger, *Microbiol. Rev.*, 53:85–108 (1989)]. Many organisms produce urease in order to generate ammonia as a source of nitrogen [D'Orazio and Collins, *J. Bacteriol.*, 175:3459–3467 (1993)]. So far, the effect of urease activity on antibiotic resistance has not been reported; no association of elevated urease activity to decreased methicillin resistance was observed in these experiments.

If femR315 was considered to be a UreC-like gene, an urease operon or gene cluster should be found in the vicinity of the femR315 region because multiple genes would be necessary for expression of urease. However, no such cluster could be detected within a region of about 1 kb upstream and 4 kb downstream of the femR315 (data not shown). Furthermore, multiple sequence alignment analysis showed both *Mycobacterium leprae* UreD and *Helicobacter pylori* UreC share the similar critical amino acid stretches for PGM or PMM activity with rabbit muscle PGM and *Escherichia coli* PGM, as well as *Pseudomonas aeruginosa* PMM. These data suggest that the function of *Mycobacterium leprae* UreD and *Helicobacter pylori* UreC should be reconsidered.

Cloning and sequencing of the femR315 region made it possible to discuss the genetic events at molecular level and the biochemical consequence in peptidoglycan synthesis caused by the inactivation of femR315 allele. Expression of femR315 gene and studies on the enzymatic function of femR315 gene product will allow further understanding of the role of femR315 gene in high-level methicillin resistance in *Staphylococcus aureaus*.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

It is also to be understood that all base pair sizes given for nucleotides and all molecular weight information for proteins are approximate and are used for the purpose of description.

Various references are cited throughout this specification, each of which is incorporated herein by reference in its entirety.

What is claimed is:

1. An isolated nucleic acid molecule encoding a protein which confers increased sensitivity to an antibiotic in *Staphylococcus aureus* to which a parent strain of the *S. aureus* is resistant, said nucleic acid molecule consisting of nucleotides located in the SmaI-I fragment of the chromosome of the *S. aureus* and having a mutation at insertion site Ω720 of the femR315 gene in the SmaI-I fragment.

2. The nucleic acid molecule of claim 1, wherein the mutation is caused by insertion of transposon Tn551.

3. The nucleic acid molecule of claim 1, wherein the SmaI-I fragment is derived from *S. aureus* strain RUSA315.

4. The nucleic acid molecule of claim 1, wherein said nucleic acid molecule consists of the nucleotides set forth in SEQ ID NO:1.

5. The nucleic acid molecule of claim 1, wherein said nucleic acid molecule encodes the amino acid sequence set forth in SEQ ID NO:2.

6. The nucleic acid molecule of claim 1, wherein the increased sensitivity is to the beta lactam antibiotic.

7. The nucleic acid molecule of claim 1, wherein the increased sensitivity is to the methicillin antibiotic.

8. An expression vector comprising the nucleic acid molecule of claim 1 operably associated with an expression control sequence.

9. A bacterial cell comprising the expression vector of claim 8.

* * * * *

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 2187 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (vi) ORIGINAL SOURCE:
        (A) ORGANISM: Staphylococcus aureus
        (B) STRAIN: RUSA 315

(xi) SEQUENCE DESCRIPTION: SEQ ID NO:1:

```
ATCGCTTATT TAAAAGCCAC TTTTAAAACT AATAAAAAGA TTAATGGTGA CACAAAAGAT      60

GTCGCAGAAG TAACGGCTTT TGATAAAAAA CTGAATAAAT TAAATGTATC GATTCAACCT     120

AATGAAGTGA ATTTACAAGT TAAAGTAGAG CCTTTTAGCA AAAAGGTTAA AGTAAATGTT     180

AAACAGAAAG GTAGTTTAGC AGATGATAAA GAGTTAAGTT CGATTGATTT AGAAGATAAA     240

GAAATTGAAA TCTTCGGTAG TCGAGATGAC TTACAAAATA TAAGCGAAGT TGATGCAGAA     300

GTAGATTTAG ATGGTATTTC AGAATCAACT GAAAAGACTG TAAAAATCAA TTTACCAGAA     360

CATGTCACTA AAGCACAACC AAGTGAAACG AAGGCTTATA TAAATGTAAA ATAAATAGCT     420

AAATTAAAGG AGAGTAAACA ATGGGAAAAT ATTTTGGTAC AGACGGAGTA AGAGGTGTCG     480

CAAACCAAGA ACTAACACCT GAATTGGCAT TTAAATTAGG AAGATACGGT GGCTATGTTC     540

TAGCACATAA TAAAGGTGAA AACACCCAC GTGTACTTGT AGGTCGCGAT ACTAGAGTTT     600

CAGGTGAAAT GTTAGAATCA GCATTAATAG CTGGTTTGAT TCAATTGGT GCAGAAGTGA     660

TGCGATTAGG TATTATTTCA ACACCAGGTG TTGCATATTT AACACGCGAT ATGGGTGCAG     720

AGTTAGGTGT AATGATTTCA GCCTCTCATA ATCCAGTTGC AGATAATGGT ATTAAATTCT     780

TTGGATCAGA TGGTTTTAAA CTATCAGATG AACAAGAAAA TGAAATTGAA GCATTATTGG     840

ATCAAGAAAA CCCAGAATTA CCAAGACCAG TTGGCAATGA TATTGTACAT TATTCAGATT     900

ACTTTGAAGG GGCACAAAAA TATTTGAGCT ATTTAAAATC AACAGTAGAT GTTAACTTTG     960

AAGGTTTGAA AATTGCTTTA GATGGCGCAA ATGGTTCAAC ATCATCACTA GCGCCATTCT    1020

TATTTGGTGA CTTAGAAGCA GATACTGAAA CAATTGGATG TAGTCCTGAT GGATATAATA    1080

TCAATGAGAA ATGTGGCTCT ACACATCCTG AAAAATTAGC TGAAAAAGTA GTTGAAACTG    1140

AAAGTGATTT TGGGTTAGCA TTTGACGGCG ATGGAGACAG AATCATAGCA GCAGATGAGA    1200

ATGGTCAAAT CGTTGACGGT GACCAAATTA TGTTTATTAT TGGTCAAGAA ATGCATAAAA    1260

ATCAAGAATT GAATAATGAC ATGATTGTTT CTACTGTTAT GAGTAATTTA GGTTTTTACA    1320

AAGCGCTTGA ACAAGAAGGA ATTAAATCTA ATAAAACTAA AGTTGGCGAC AGATATGTAG    1380

TAGAAGAAAT GCGTCGCGGT AATTATAACT TAGGTGGAGA ACAATCTGGA CATATCGTTA    1440

TGATGGATTA CAATACAACT GGTGATGGTT TATTAACTGG TATTCAATTA GCTTCTGTAA    1500

TAAAAATGAC TGGTAAATCA CTAAGTGAAT TAGCTGGACA AATGAAAAAA TATCCACAAT    1560

CATTAATTAA CGTACGCGTA ACAGATAAAT ATCGTGTTGA AGAAAATGTT GACGTTAAAG    1620

AAGTTATGAC TAAAGTAGAA GTAGAAATGA ATGGAGAAGG TCGAATTTTA GTAAGACCTT    1680

CTGGAACAGA ACCATTAGTT CGTGTCATGG TTGAAGCAGC AACTGATGAA GATGCTGAAA    1740

GATTTGCACA ACAAATAGCT GATGTGGTTC AAGATAAAAT GGGATTAGAT AAATAAATAC    1800

TGTATTACAA ATGAGCCGAT GCGTATGCAT CGGTTTTTTG TGTTTGTAGA AATAATTTAT    1860

AGTACAAACG TAAAATGATA TAAACAAAAT AAAAACAAAG TAATCAATAT GTAATATAAA    1920

ATACACTGGT ACTCAATATA TAATGATGAT AAAATTAATT TTAATTAGAT AGAGTTGCTT    1980

TGTGTTTTTA ACGCAGATGC TACTACTTAT CTTAACAGTT GATTAAGTGA AATCATTTAA    2040

CAGCGAGAAT AATCAACCAG GAGGATGACT TAATGAATTT ATTCAGACAA CAAAAATTTA    2100
```

-continued

```
GTATCAGAAA ATTTAATGTC GGTATTTTTT CAGCTTTAAT TGCCACTGTT ACTTTTATAT    2160

CTACTAACCC GACAACAGCG TCTGCAG                                        2187
```

(2) INFORMATION FOR SEQ ID NO:2:

(i) SEQUENCE CHARACTERISTICS:
        (A) LENGTH: 451 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Staphylococcus aureus
        (B) STRAIN: RUSA 315

(xi) SEQUENCE DESCRIPTION: SEQ ID NO:2:

```
Met Gly Lys Tyr Phe Gly Thr Asp Gly Val Arg Gly Val Ala Asn Gln
1               5                   10                  15

Glu Leu Thr Pro Glu Leu Ala Phe Lys Leu Gly Arg Tyr Gly Gly Tyr
            20                  25                  30

Val Leu Ala His Asn Lys Gly Glu Lys His Pro Arg Val Leu Val Gly
        35                  40                  45

Arg Asp Thr Arg Val Ser Gly Glu Met Leu Glu Ser Ala Leu Ile Ala
    50                  55                  60

Gly Leu Ile Ser Ile Gly Ala Glu Val Met Arg Leu Gly Ile Ile Ser
65                  70                  75                  80

Thr Pro Gly Val Ala Tyr Leu Thr Arg Asp Met Gly Ala Glu Leu Gly
                85                  90                  95

Val Met Ile Ser Ala Ser His Asn Pro Val Ala Asp Asn Gly Ile Lys
            100                 105                 110

Phe Phe Gly Ser Asp Gly Phe Lys Leu Ser Asp Glu Gln Glu Asn Glu
        115                 120                 125

Ile Glu Ala Leu Leu Asp Gln Glu Asn Pro Glu Leu Pro Arg Pro Val
    130                 135                 140

Gly Asn Asp Ile Val His Tyr Ser Asp Tyr Phe Glu Gly Ala Gln Lys
145                 150                 155                 160

Tyr Leu Ser Tyr Leu Lys Ser Thr Val Asp Val Asn Phe Glu Gly Leu
                165                 170                 175

Lys Ile Ala Leu Asp Gly Ala Asn Gly Ser Thr Ser Ser Leu Ala Pro
            180                 185                 190

Phe Leu Phe Gly Asp Leu Glu Ala Asp Thr Glu Thr Ile Gly Cys Ser
        195                 200                 205

Pro Asp Gly Tyr Asn Ile Asn Glu Lys Cys Gly Ser Thr His Pro Glu
    210                 215                 220

Lys Leu Ala Glu Lys Val Val Glu Thr Glu Ser Asp Phe Gly Leu Ala
225                 230                 235                 240

Phe Asp Gly Asp Gly Asp Arg Ile Ile Ala Ala Asp Glu Asn Gly Gln
                245                 250                 255

Ile Val Asp Gly Asp Gln Ile Met Phe Ile Ile Gly Gln Glu Met His
            260                 265                 270

Lys Asn Gln Glu Leu Asn Asn Asp Met Ile Val Ser Thr Val Met Ser
        275                 280                 285

Asn Leu Gly Phe Tyr Lys Ala Leu Glu Gln Glu Gly Ile Lys Ser Asn
    290                 295                 300
```

```
Lys Thr Lys Val Gly Asp Arg Tyr Val Glu Glu Met Arg Arg Gly
305                 310                 315                 320

Asn Tyr Asn Leu Gly Gly Glu Gln Ser Gly His Ile Val Met Met Asp
            325                 330                 335

Tyr Asn Thr Thr Gly Asp Gly Leu Leu Thr Gly Ile Gln Leu Ala Ser
                340                 345                 350

Val Ile Lys Met Thr Gly Lys Ser Leu Ser Glu Leu Ala Gly Gln Met
            355                 360                 365

Lys Lys Tyr Pro Gln Ser Leu Ile Asn Val Arg Val Thr Asp Lys Tyr
            370                 375                 380

Arg Val Glu Glu Asn Val Asp Val Lys Glu Val Met Thr Lys Val Glu
385                 390                 395                 400

Val Glu Met Asn Gly Glu Gly Arg Ile Leu Val Arg Pro Ser Gly Thr
                405                 410                 415

Glu Pro Leu Val Arg Val Met Val Glu Ala Ala Thr Asp Glu Asp Ala
            420                 425                 430

Glu Arg Phe Ala Gln Gln Ile Ala Asp Val Val Gln Asp Lys Met Gly
            435                 440                 445

Leu Asp Lys
    450

(2) INFORMATION FOR SEQ ID NO:3:

(i) SEQUENCE CHARACTERISTICS:
        (A) LENGTH: 445 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:3:

Met Lys Ile Phe Gly Thr Asp Gly Val Arg Gly Lys Ala Gly Val Lys
1               5                   10                  15

Leu Thr Pro Met Phe Val Met Arg Leu Gly Ile Ala Ala Gly Leu Tyr
                20                  25                  30

Phe Lys Lys His Ser Gln Thr Asn Lys Ile Leu Ile Gly Lys Asp Thr
            35                  40                  45

Arg Lys Ser Gly Tyr Met Val Glu Asn Ala Leu Val Ser Ala Leu Thr
        50                  55                  60

Ser Ile Gly Tyr Asn Val Ile Gln Ile Gly Pro Met Pro Thr Pro Ala
65                  70                  75                  80

Ile Ala Phe Leu Thr Glu Asp Met Arg Cys Asp Ala Gly Ile Met Ile
                85                  90                  95

Ser Ala Ser His Asn Pro Phe Glu Asp Asn Gly Ile Lys Phe Phe Asn
            100                 105                 110

Ser Tyr Gly Tyr Lys Leu Lys Glu Glu Glu Arg Ala Ile Glu Glu
            115                 120                 125

Ile Phe His Asp Glu Gly Leu Leu His Ser Ser Tyr Lys Val Gly Glu
130                 135                 140

Ser Val Gly Ser Ala Lys Arg Ile Asp Asp Val Ile Gly Arg Tyr Ile
145                 150                 155                 160

Ala His Leu Lys His Ser Phe Pro Lys His Leu Asn Leu Gln Ser Leu
                165                 170                 175
```

```
Arg Ile Val Leu Asp Thr Ala Asn Gly Ala Ala Tyr Lys Val Ala Pro
            180                 185                 190

Val Val Phe Ser Glu Leu Gly Ala Asp Val Leu Val Ile Asn Asp Glu
            195                 200                 205

Pro Asn Gly Cys Asn Ile Asn Glu Gln Cys Gly Ala Leu His Pro Asn
            210                 215                 220

Gln Leu Ser Gln Glu Val Lys Lys Tyr Arg Ala Asp Leu Gly Phe Ala
225                 230                 235                 240

Phe Asp Gly Asp Ala Asp Arg Leu Val Val Asp Asn Leu Gly Asn
                245                 250                 255

Ile Val His Gly Asp Lys Leu Leu Gly Val Leu Gly Val Tyr Gln Lys
            260                 265                 270

Ser Lys Asn Ala Leu Ser Ser Gln Ala Ile Val Ala Thr Asn Met Ser
            275                 280                 285

Asn Leu Ala Leu Lys Glu Tyr Leu Lys Ser Gln Asp Leu Glu Leu Lys
            290                 295                 300

His Cys Ala Ile Gly Asp Lys Phe Val Ser Glu Cys Met Arg Leu Asn
305                 310                 315                 320

Lys Ala Asn Phe Gly Gly Glu Gln Ser Gly His Ile Ile Phe Ser Asp
                325                 330                 335

Tyr Ala Lys Thr Gly Asp Gly Leu Val Cys Ala Leu Gln Val Ser Ala
            340                 345                 350

Leu Val Leu Glu Ser Lys Leu Val Ser Ser Val Arg Leu Asn Pro Phe
            355                 360                 365

Glu Leu Tyr Pro Gln Asn Leu Val Asn Leu Asn Val Gln Lys Lys Pro
            370                 375                 380

Pro Leu Glu Ser Leu Lys Gly Tyr Asn Ala Leu Leu Lys Glu Leu Asp
385                 390                 395                 400

Lys Leu Glu Ile Arg His Leu Ile Arg Tyr Ser Gly Thr Glu Asn Lys
                405                 410                 415

Leu Arg Ile Leu Leu Glu Ala Lys Asp Glu Lys Leu Leu Glu Ser Lys
            420                 425                 430

Met Gln Glu Leu Lys Glu Phe Phe Glu Gly His Leu Cys
            435                 440                 445

(2) INFORMATION FOR SEQ ID NO:4:

(i) SEQUENCE CHARACTERISTICS:
        (A) LENGTH: 463 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:4:

Met Gly Arg Leu Phe Gly Thr Asp Gly Val Arg Gly Val Ala Asn Arg
1               5                   10                  15

Glu Leu Thr Pro Glu Leu Val Leu Ala Leu Gly Ala Ala Ala Ala Arg
            20                  25                  30

Cys Leu Ala Asn Ser Gly Glu Pro Gly Arg Arg Val Ala Val Ile Gly
            35                  40                  45

Arg Asp Pro Arg Ala Ser Gly Glu Met Leu Glu Ala Ala Val Ile Ala
            50                  55                  60

Gly Leu Thr Ser Ala Gly Val Asp Ala Leu Arg Val Gly Val Leu Pro
```

```
-continued
65                  70                  75                  80
Thr Pro Ala Val Ala Tyr Leu Thr Gly Ala Tyr Asp Ala Asp Phe Gly
                    85                  90                  95

Val Met Ile Ser Ala Ser His Asn Pro Met Val Asp Asn Gly Ile Lys
                100                 105                 110

Ile Phe Gly Pro Gly Gly His Lys Leu Asp Asp Thr Glu Asp Gln
            115                 120                 125

Ile Glu Asp Leu Val Thr Gly Pro Gly Leu Arg Pro Ala Gly Val
        130                 135                 140

Ala Ile Gly Arg Val Ile Asp Ala Glu Asp Ala Thr Glu Arg Tyr Leu
145                 150                 155                 160

Arg His Val Gly Lys Ala Ser Thr Ile Arg Leu Asp Gly Leu Thr Val
                165                 170                 175

Val Val Asp Cys Ala His Gly Ala Ala Ser Ser Ala Ala Pro Arg Ala
                180                 185                 190

Tyr Arg Ala Ala Gly Ala Arg Val Ile Ala Ile Asn Ala Asp Pro Asn
                195                 200                 205

Gly Ile Asn Ile Asn Asp Arg Cys Gly Ser Thr Asp Leu Gly Ser Leu
            210                 215                 220

Arg Ser Ala Val Leu Ala His Arg Ala Asp Leu Gly Leu Ala His Asp
225                 230                 235                 240

Gly Asp Ala Asp Arg Cys Leu Ala Val Asp Ala Asn Gly Asp Leu Val
                245                 250                 255

Asp Gly Asp Ala Ile Met Val Val Leu Ala Leu Ala Met Gln Glu Ala
                260                 265                 270

Gly Glu Leu Ser Ser Asn Thr Leu Val Thr Thr Val Met Ser Asn Leu
            275                 280                 285

Gly Leu His Leu Ala Met Arg Ser Val Gly Val Ile Val Arg Thr Thr
            290                 295                 300

Asp Val Gly Asp Arg Tyr Val Leu Glu Glu Leu Arg Ala Gly Asp Phe
305                 310                 315                 320

Ser Leu Gly Gly Glu Gln Ser Gly His Ile Val Met Pro Ala Leu Gly
                325                 330                 335

Ser Thr Gly Asp Gly Ile Ile Thr Gly Leu Arg Leu Met Thr Arg Met
            340                 345                 350

Val Gln Thr Ser Ser Ser Leu Ala Ala Leu Ala Ser Ala Met Arg Ala
            355                 360                 365

Leu Pro Gln Val Leu Ile Asn Val Glu Val Ala Asp Lys Thr Thr Ala
            370                 375                 380

Ala Ala Ala Pro Leu Val Gln Thr Ala Val Glu Thr Ala Glu Val Glu
385                 390                 395                 400

Leu Gly Asn Thr Gly Arg Ile Leu Leu Arg Pro Ser Gly Thr Glu Pro
                405                 410                 415

Met Ile Arg Val Met Val Glu Ala Ala Glu Glu Asp Val Ala His Arg
                420                 425                 430

Val Ala Thr Arg Val Ala Ala Ala Val Ser Ala Gln Gly Ser Pro Leu
                435                 440                 445

Arg Cys Trp Asn Pro Asp Ala Ile Ser Gly Val Glu Leu Arg Leu
            450                 455                 460
```

(2) INFORMATION FOR SEQ ID NO:5:

(i) SEQUENCE CHARACTERISTICS:
        (A) LENGTH: 455 amino acids (B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:5:

```
Met Lys Lys Leu Thr Cys Phe Lys Ala Tyr Asp Ile Arg Gly Lys Leu
 1               5                  10                  15
Gly Glu Glu Leu Asn Glu Asp Ile Ala Trp Arg Ile Gly Arg Ala Tyr
                20                  25                  30
Gly Glu Phe Leu Lys Pro Lys Thr Ile Val Leu Gly Gly Asp Val Arg
            35                  40                  45
Leu Thr Ser Glu Thr Leu Lys Leu Ala Leu Ala Lys Gly Leu Gln Asp
50                  55                  60
Ala Gly Val Asp Val Leu Asp Ile Gly Met Ser Gly Thr Glu Glu Ile
65                  70                  75                  80
Tyr Phe Ala Thr Phe His Leu Gly Val Asp Gly Gly Ile Glu Val Thr
                85                  90                  95
Ala Ser His Asn Pro Met Asp Tyr Asn Gly Met Lys Leu Val Arg Glu
                100                 105                 110
Gly Ala Arg Pro Ile Ser Gly Asp Thr Gly Leu Arg Asp Val Gln Arg
            115                 120                 125
Leu Ala Glu Ala Asn Asp Phe Pro Pro Val Asp Glu Thr Lys Arg Gly
130                 135                 140
Arg Tyr Gln Gln Ile Asn Leu Arg Asp Ala Tyr Val Asp His Leu Phe
145                 150                 155                 160
Gly Tyr Ile Asn Val Lys Asn Leu Thr Pro Leu Lys Leu Val Ile Asn
                165                 170                 175
Ser Gly Asn Gly Ala Ala Gly Pro Val Val Asp Ala Ile Glu Ala Arg
                180                 185                 190
Phe Lys Ala Leu Gly Ala Pro Val Glu Leu Ile Lys Val His Asn Thr
            195                 200                 205
Pro Asp Gly Asn Phe Pro Asn Gly Ile Pro Asn Pro Leu Leu Pro Glu
210                 215                 220
Cys Arg Asp Asp Thr Arg Asn Ala Val Ile Lys His Gly Ala Asp Met
225                 230                 235                 240
Gly Ile Ala Phe Asp Gly Asp Phe Asp Arg Cys Phe Leu Phe Asp Glu
                245                 250                 255
Lys Gly Gln Phe Ile Glu Gly Tyr Tyr Ile Val Gly Leu Leu Ala Glu
                260                 265                 270
Ala Phe Leu Glu Lys Asn Pro Gly Ala Lys Ile Ile His Asp Pro Arg
            275                 280                 285
Leu Ser Trp Asn Thr Val Asp Val Val Thr Ala Ala Gly Gly Thr Pro
290                 295                 300
Val Met Ser Lys Thr Gly His Ala Phe Ile Lys Glu Arg Met Arg Lys
305                 310                 315                 320
Glu Asp Ala Ile Tyr Gly Gly Glu Met Ser Ala His His Tyr Phe Arg
                325                 330                 335
Asp Phe Ala Tyr Cys Asp Ser Gly Met Ile Pro Trp Leu Leu Val Ala
            340                 345                 350
Glu Leu Val Cys Leu Lys Asp Lys Thr Leu Gly Glu Leu Val Arg Asp
            355                 360                 365
```

```
Arg Met Ala Ala Phe Pro Ala Ser Gly Glu Ile Asn Ser Lys Leu Ala
    370                 375                 380

Gln Pro Val Glu Ala Ile Asn Val Glu Gln His Phe Ser Arg Glu Ala
385                 390                 395                 400

Leu Ala Val Asp Arg Thr Asp Gly Ile Ser Met Thr Phe Ala Asp Trp
                405                 410                 415

Arg Phe Asn Leu Arg Thr Ser Asn Thr Glu Pro Val Val Arg Leu Asn
            420                 425                 430

Val Glu Ser Arg Gly Asp Val Pro Leu Met Glu Ala Arg Thr Arg Thr
        435                 440                 445

Leu Leu Thr Leu Leu Asn Glu
    450                 455

(2) INFORMATION FOR SEQ ID NO:6:

(i) SEQUENCE CHARACTERISTICS:
        (A) LENGTH: 456 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:6:

Met Thr Lys Leu Thr Cys Phe Lys Ala Tyr Asp Ile Arg Gly Arg Leu
1               5                   10                  15

Gly Glu Glu Leu Asn Glu Asp Ile Ala Trp Arg Ile Gly Arg Ala Tyr
                20                  25                  30

Gly Glu Tyr Leu Lys Pro Lys Thr Val Val Leu Gly Gly Asp Val Arg
            35                  40                  45

Leu Thr Ser Glu Ala Leu Asn Val Ala Leu Ala Lys Gly Leu Gln Asp
        50                  55                  60

Ala Gly Val Asp Val Leu Asp Ile Gly Met Ser Gly Thr Glu Glu Ile
65                  70                  75                  80

Tyr Phe Ala Thr Phe His Leu Gly Val Asp Gly Gly Ile Glu Val Thr
                85                  90                  95

Ala Ser His Asn Pro Met Asp Tyr Asn Gly Met Lys Leu Val Arg Glu
            100                 105                 110

Gly Ala Arg Pro Ile Ser Gly Asp Thr Gly Leu Arg Asp Val Gln Arg
        115                 120                 125

Leu Ala Glu Ala Gly Asp Phe Pro Pro Val Asn Glu Ala Ala Arg Gly
    130                 135                 140

Ser Tyr Arg Gln Ile Ser Leu Arg Asp Ala Tyr Ile Asp His Leu Leu
145                 150                 155                 160

Gly Tyr Ile Ser Val Asn Asn Leu Thr Pro Leu Lys Leu Val Phe Asn
                165                 170                 175

Ala Gly Asn Gly Ala Ala Gly Pro Val Ile Asp Ala Ile Glu Ala Arg
            180                 185                 190

Leu Lys Ala Leu Gly Ala Pro Val Glu Phe Ile Lys Ile His Asn Thr
        195                 200                 205

Pro Asp Gly Thr Phe Pro Asn Gly Ile Pro Asn Pro Leu Leu Pro Glu
    210                 215                 220

Cys Arg Asp Asp Thr Arg Lys Ala Val Ile Glu His Gly Ala Asp Met
225                 230                 235                 240

Gly Ile Ala Phe Asp Gly Asp Phe Asp Arg Cys Phe Leu Phe Asp Glu
```

```
                       245                 250                 255
Lys Gly Gln Phe Ile Glu Gly Tyr Tyr Ile Val Gly Leu Leu Ala Glu
            260                 265                 270

Ala Phe Leu Glu Lys His Pro Gly Ala Lys Ile Ile His Asp Pro Arg
            275                 280                 285

Leu Thr Trp Asn Thr Glu Ala Val Val Thr Ala Ala Gly Gly Thr Pro
            290                 295                 300

Val Met Ser Lys Thr Gly His Ala Phe Ile Lys Glu Arg Met Arg Thr
305                 310                 315                 320

Glu Asp Ala Ile Tyr Gly Gly Glu Met Ser Ala His His Tyr Phe Arg
                325                 330                 335

Asp Phe Ala Tyr Cys Asp Ser Gly Met Ile Pro Trp Leu Leu Val Ala
                340                 345                 350

Glu Leu Val Cys Leu Lys Arg Gln Ser Leu Gly Glu Leu Val Arg Asp
                355                 360                 365

Arg Met Ala Ala Phe Pro Ala Ser Gly Glu Ile Asn Ser Arg Leu Ala
            370                 375                 380

Glu Pro Ala Ala Ala Ile Ala Arg Val Glu Ala His Phe Ala Glu Glu
385                 390                 395                 400

Ala Gln Ala Val Asp Arg Thr Asp Gly Leu Ser Met Ser Phe Ala Asp
                405                 410                 415

Trp Arg Phe Asn Leu Arg Ser Ser Asn Thr Glu Pro Val Val Arg Leu
                420                 425                 430

Asn Val Glu Ser Arg Gly Asp Ile Pro Leu Met Glu Ala Arg Thr Arg
                435                 440                 445

Thr Leu Leu Ala Leu Leu Asn Gln
        450                 455

(2) INFORMATION FOR SEQ ID NO:7:

(i) SEQUENCE CHARACTERISTICS:
        (A) LENGTH: 561 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:7:

Val Lys Ile Val Thr Val Lys Thr Lys Ala Tyr Pro Asp Gln Lys Pro
1               5                   10                  15

Gly Thr Ser Gly Leu Arg Lys Arg Val Lys Val Phe Gln Ser Ser Thr
            20                  25                  30

Asn Tyr Ala Glu Asn Phe Ile Gln Ser Ile Ile Ser Thr Val Glu Pro
        35                  40                  45

Ala Gln Arg Gln Glu Ala Thr Leu Val Val Gly Gly Asp Gly Arg Phe
    50                  55                  60

Tyr Met Lys Glu Ala Ile Gln Leu Ile Val Arg Ile Ala Ala Ala Asn
65                  70                  75                  80

Gly Ile Gly Arg Leu Val Ile Gly Gln Asn Gly Ile Leu Ser Thr Pro
            85                  90                  95

Ala Val Ser Cys Ile Ile Arg Lys Ile Lys Ala Ile Gly Gly Ile Ile
            100                 105                 110

Leu Thr Ala Ser His Asn Pro Gly Gly Pro Asn Gly Asp Phe Gly Ile
            115                 120                 125
```

-continued

```
Lys Phe Asn Ile Ser Asn Gly Gly Pro Ala Pro Glu Ala Ile Thr Asp
    130                 135                 140
Lys Ile Phe Gln Ile Ser Lys Thr Ile Glu Glu Tyr Ala Ile Cys Pro
145                 150                 155                 160
Asp Leu Lys Val Asp Leu Gly Val Leu Gly Lys Gln Gln Phe Asp Leu
                165                 170                 175
Glu Asn Lys Phe Lys Pro Phe Thr Val Glu Ile Val Asp Ser Val Glu
            180                 185                 190
Ala Tyr Ala Thr Met Leu Arg Asn Ile Phe Asp Phe Asn Ala Leu Lys
        195                 200                 205
Glu Leu Leu Ser Gly Pro Asn Arg Leu Lys Ile Arg Ile Asp Ala Met
    210                 215                 220
His Gly Val Val Gly Pro Tyr Val Lys Lys Ile Leu Cys Glu Glu Leu
225                 230                 235                 240
Gly Ala Pro Ala Asn Ser Ala Val Asn Cys Val Pro Leu Glu Asp Phe
                245                 250                 255
Gly Gly His His Pro Asp Pro Asn Leu Thr Tyr Ala Ala Asp Leu Val
            260                 265                 270
Glu Thr Met Lys Ser Gly Glu His Asp Phe Gly Ala Ala Phe Asp Gly
        275                 280                 285
Asp Gly Asp Arg Asn Met Ile Leu Gly Lys His Gly Phe Phe Val Asn
    290                 295                 300
Pro Ser Asp Ser Val Ala Val Ile Ala Ala Asn Ile Phe Ser Ile Pro
305                 310                 315                 320
Tyr Phe Gln Gln Thr Gly Val Arg Gly Phe Ala Arg Ser Met Pro Thr
                325                 330                 335
Ser Gly Ala Leu Asp Arg Val Ala Asn Ala Thr Lys Ile Ala Leu Tyr
            340                 345                 350
Glu Thr Pro Thr Gly Trp Lys Phe Phe Gly Asn Leu Met Asp Ala Ser
        355                 360                 365
Lys Leu Ser Leu Cys Gly Glu Glu Ser Phe Gly Thr Gly Ser Asp His
    370                 375                 380
Ile Arg Glu Lys Asp Gly Leu Trp Ala Val Leu Ala Trp Leu Ser Ile
385                 390                 395                 400
Leu Ala Thr Arg Lys Gln Ser Val Glu Asp Ile Leu Lys Asp His Trp
                405                 410                 415
His Lys Phe Gly Arg Asn Phe Phe Thr Arg Tyr Asp Tyr Glu Glu Val
            420                 425                 430
Glu Ala Glu Gly Ala Thr Lys Met Met Lys Asp Leu Glu Ala Leu Met
        435                 440                 445
Phe Asp Arg Ser Phe Val Gly Lys Gln Phe Ser Ala Asn Asp Lys Val
    450                 455                 460
Tyr Thr Val Glu Lys Ala Asp Asn Phe Glu Tyr His Asp Pro Val Asp
465                 470                 475                 480
Gly Ser Val Ser Lys Asn Gln Gly Leu Arg Leu Ile Phe Ala Asp Gly
                485                 490                 495
Ser Arg Ile Ile Phe Arg Leu Ser Gly Thr Gly Ser Ala Gly Ala Thr
            500                 505                 510
Ile Arg Leu Tyr Ile Asp Ser Tyr Glu Lys Asp Asn Ala Lys Ile Asn
        515                 520                 525
Gln Asp Pro Gln Val Met Leu Ala Pro Leu Ile Ser Ile Ala Leu Lys
    530                 535                 540
```

Val Ser Gln Leu Gln Glu Arg Thr Gly Arg Thr Ala Pro Thr Val Ile
545                 550                 555                 560

Thr (2) INFORMATION FOR SEQ ID NO:8:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (iii) HYPOTHETICAL: NO (vi) ORIGINAL SOURCE:
        (A) ORGANISM: Staphylococcus aureus
        (B) STRAIN: RUSA 315

(xi) SEQUENCE DESCRIPTION: SEQ ID NO:8:

Ala Glu Leu Gly Val Met Ile Ser Ala Ser His Asn Pro Val Ala Asp
1               5                   10                  15

Asn Gly Ile Lys Phe
            20

(2) INFORMATION FOR SEQ ID NO:9:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:9:

Ala Ile Gly Gly Ile Ile Leu Thr Ala Ser His Asn Pro Gly Gly Pro
1               5                   10                  15

Asn Gly Asp Phe Gly
            20

(2) INFORMATION FOR SEQ ID NO:10:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (vi) ORIGINAL SOURCE:
        (A) ORGANISM: Staphylococcus aureus
        (B) STRAIN: RUSA 315

(xi) SEQUENCE DESCRIPTION: SEQ ID NO:10:

Glu Lys Cys Gly Ser Thr His Pro Glu Lys
1               5                   10

(2) INFORMATION FOR SEQ ID NO:11:

(i) SEQUENCE CHARACTERISTICS:
        (A) LENGTH: 10 amino acids
        (B) TYPE: amino acid (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:11:

Glu Asp Phe Gly Gly His His Pro Asp Pro
1               5                   10

(2) INFORMATION FOR SEQ ID NO:12:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (iii) HYPOTHETICAL: NO (vi) ORIGINAL SOURCE:
        (A) ORGANISM: Staphylococcus aureus
        (B) STRAIN: RUSA 315

(xi) SEQUENCE DESCRIPTION: SEQ ID NO:12:

Asp Phe Gly Leu Ala Phe Asp Gly Asp Gly Asp Arg Ile Ile
1               5                   10

(2) INFORMATION FOR SEQ ID NO:13:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:13:

Asp Phe Gly Ala Ala Phe Asp Gly Asp Gly Asp Arg Asn Met
1               5                   10

(2) INFORMATION FOR SEQ ID NO:14:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (iii) HYPOTHETICAL: NO (vi) ORIGINAL SOURCE:
        (A) ORGANISM: Staphylococcus aureus
        (B) STRAIN: RUSA 315

(xi) SEQUENCE DESCRIPTION: SEQ ID NO:14:

Gly Asn Tyr Asn Leu Gly Gly Glu Gln Ser Gly His Ile
1               5                   10

(2) INFORMATION FOR SEQ ID NO:15:

(i) SEQUENCE CHARACTERISTICS:
        (A) LENGTH: 13 amino acids

```
            (B) TYPE: amino acid
            (C) STRANDEDNESS: single
            (D) TOPOLOGY: linear (ii) MOLECULE TYPE: peptide (iii) HYPOTHETICAL: NO (xi) SEQUENCE DESCRIPTION: SEQ ID NO:15:

Ser Lys Leu Ser Leu Cys Gly Glu Glu Ser Phe Gly Thr
1               5                   10

(2) INFORMATION FOR SEQ ID NO:16:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (iii) HYPOTHETICAL: NO (vi) ORIGINAL SOURCE:
            (A) ORGANISM: Staphylococcus aureus
            (B) STRAIN: RUSA 315

(xi) SEQUENCE DESCRIPTION: SEQ ID NO:16:

Thr Thr Gly Asp Gly Leu Leu Thr Gly Ile
1               5                   10

(2) INFORMATION FOR SEQ ID NO:17:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (iii) HYPOTHETICAL: NO (xi) SEQUENCE DESCRIPTION: SEQ ID NO:17:

Arg Glu Lys Asp Gly Leu Trp Ala Val Leu
1               5                   10
```